US010920238B2

(12) United States Patent
Meesapyodsuk et al.

(10) Patent No.: US 10,920,238 B2
(45) Date of Patent: Feb. 16, 2021

(54) WINTER ACONITE FATTY ACID ELONGASE AND USES THEREOF IN THE PRODUCTION OF FATTY ACIDS

(71) Applicant: National Research Council of Canada, Ottawa (CA)

(72) Inventors: Dauenpen Meesapyodsuk, Saskatoon (CA); Xiao Qiu, Saskatoon (CA); Bob Chapman, Stratford (CA)

(73) Assignee: National Research Council of Canada

( * ) Notice: Subject to any disclaimer, the term of this patent is extended or adjusted under 35 U.S.C. 154(b) by 228 days.

(21) Appl. No.: 16/305,609

(22) PCT Filed: May 31, 2017

(86) PCT No.: PCT/IB2017/053208

§ 371 (c)(1),
(2) Date: Nov. 29, 2018

(87) PCT Pub. No.: WO2017/208173

PCT Pub. Date: Dec. 7, 2017

(65) Prior Publication Data

US 2020/0325488 A1 Oct. 15, 2020

Related U.S. Application Data

(60) Provisional application No. 62/344,071, filed on Jun. 1, 2016.

(51) Int. Cl.

| | |
|---|---|
| ***C12N 15/82*** | (2006.01) |
| ***A23L 33/115*** | (2016.01) |
| ***A23D 9/02*** | (2006.01) |
| ***C12P 7/64*** | (2006.01) |
| ***C12N 9/10*** | (2006.01) |

(52) U.S. Cl.

CPC ........... *C12N 15/8247* (2013.01); *A23D 9/02* (2013.01); *A23L 33/115* (2016.08); *C12N 9/1029* (2013.01); *C12N 15/8218* (2013.01); *C12P 7/6409* (2013.01); *C12Y 203/01099* (2013.01)

(58) Field of Classification Search

CPC .......................... C12N 15/8247; C12N 9/1029

See application file for complete search history.

(56) References Cited

U.S. PATENT DOCUMENTS

| | | | |
|---|---|---|---|
| 8,188,335 B2 | 5/2012 | Pereira et al. | |
| 8,933,300 B2 | 1/2015 | Heinz et al. | |
| 9,068,213 B2 | 6/2015 | Franklin et al. | |
| 2004/0049805 A1 | 3/2004 | Lerchl et al. | |
| 2004/0053379 A1 | 3/2004 | Lerchl et al. | |
| 2008/0194685 A1 | 8/2008 | Damude et al. | |
| 2013/0160169 A1 * | 6/2013 | Qiu ...................... | C12N 9/0071 800/320.1 |

FOREIGN PATENT DOCUMENTS

| | | |
|---|---|---|
| WO | 2013158938 A1 | 10/2013 |

OTHER PUBLICATIONS

BCYL04H02 Black cohosh young leaf library (BCYL) *Actaea racemosa* cDNA 5', mRNA sequence GenBank: HO116870.1 (Year: 2011).*

Spiering, Martin J., et al. "Gene identification in black cohosh (*Actaea racemosa* L.): expressed sequence tag profiling and genetic screening yields candidate genes for production of bioactive secondary metabolites." Plant cell reports 30.4 (2011): 613-629. (Year: 2011).*

Aitzetmuller, An Unusual Fatty Acid Pattern in Eranthis Seed Oil, Lipids, 1996, 31(2): 201-205, AOCS Press.

Altschul et al., Basic Local Alignment Search Tool, Journal of Molecular Biology, 1990, 215:403-410, Academic Press Limited.

Spiering et al., BCYL04H02 Black cohosh young leaf library (BCYL) *Actaea racemosa* cDNA 5', mRNA sequence, GenBank Accession No. HO116870.1.

Henry et al., Antioxidant and Cyclooxygenase Activities of Fatty Acids Found in Food, Journal of Agricultural and Food Chemistry, 2002, 50: 2231-2234, American Chemical Society.

Mizushina et al., Inhibitory action of polyunsaturated fatty acids on IMP dehydrogenase, Biochimie, 2007, 89:581-590, ScienceDirect.

Spiering et al., Gene identification in black cohosh (*Actaea racemosa* L.): expressed sequence tag profiling and genetic screening yields candidate genes for production of bioactive secondary metabolites, Plant Cell Reports, 2011, 30(4): 613-629, Springer.

Yonezawa et al., Inhibitory action of C22-fatty acids on DNA polymerases and DNA topoisomerases, International Journal of Molecular Medicine, 2006, 18:583-588.

Jie et al., Epoxidation Reactions of Unsaturated Fatty Esters and Potassium Peroxomonosulfate, Lipids, 1998, 33(6):633-637, AOCS Press.

Jie et al., Fatty Acids, fatty acid analogues and their derivatives, Natural Product Reports, 1998, 607-629.

Mietkiewska et al., Eranthis hyemalis 3-ketoacyl-CoA synthase mRNA, complete cds, 2007, GenBank Accession No. EF682061.1.

Mietkiewska et al., Isolation and Characterization of a fatty acid elongase from *Eranthis hyemalis* seeds, UniProtKB/TrEMBL Accession No. A7L830.

* cited by examiner

*Primary Examiner* — Shubo (Joe) Zhou
*Assistant Examiner* — Lee A Visone
(74) *Attorney, Agent, or Firm* — Jessica Smith

(57) ABSTRACT

Fatty acids, and methods for the production thereof, are provided. Transgenic organisms, microbes, plants, seeds, and cells useful in the production of fatty acids, along with related expression vectors, phages, plasmids, nucleic acids, and enzymes, are also provided. Methods for the production of fatty acids such as docosadienoic acid and docosatrienoic acid, involving the use of winter aconite (*Eranthis hyemalis*) EhELO1 elongase, are described in detail.

20 Claims, 9 Drawing Sheets

Specification includes a Sequence Listing.

WINTER ACONITE FATTY ACID ELONGASE AND USES THEREOF IN THE PRODUCTION OF FATTY ACIDS

CROSS-REFERENCE TO RELATED APPLICATIONS

This application is a national phase entry of International Patent Application PCT/IB2017/053208 filed May 31, 2017, which claims the benefit of U.S. Provisional Patent Application Ser. No. 62/344,071 filed Jun. 1, 2016.

FIELD OF INVENTION

The present invention relates generally to fatty acids, and the production thereof. More specifically, the present invention relates to long and very long chain unsaturated fatty acids such as docosadienoic acid (DDA) and docosatrienoic acid (DTA), as well as transgenic organisms, plants, seeds, cells, expression vectors, phages, plasmids, nucleic acids, and enzymes relating to the production thereof.

BACKGROUND

Very long chain-polyunsaturated fatty acids (VLC-PUFAs or VLCPUFAs) are components of the cell membrane, and precursors for biologically active compounds in humans and animals. Dietary supplementation of VLCPUFAs has been suggested to provide protection against chronic diseases, to enhance the performance of eyes and brains, and to promote overall health and wellbeing of humans and animals. However, the traditional VLCPUFA market is primarily focused on a few omega-3 and omega-6 VLCPUFAs such as eicosapentaenoic acid (20:5n-3, EPA), docosahexaenoic acid (22:6n-3, DHA) and arachidonic acid (20:4n-6, ARA).

Docosadienoic acid (22:2n-6, DDA) is an omega-6 fatty acid which is 22 carbons in length and has two cis double bonds at positions 13 and 16. It has recently been reported that this fatty acid may be a strong inhibitor of mammalian DNA polymerase and topoisomerase (Yonezawa et al., 2006, Intern J Mol Medicine 18:583-588), two critical enzymes for DNA replication, repair, and recombination involved in cancer development and progression. In addition, it has also been suggested that this fatty acid has inhibitory activity towards human Type II cyclooxygenase enzyme (COX-II), a major isoform responsible for induced inflammation. Potential anti-inflammatory and anti-proliferating properties, for example, make this fatty acid an attractive target for VLCPUFA nutraceuticals (Henry et al., 2002, J Agri Food Chem, 50:2231-2234) and has indicated that DDA may have potential as an antioxidant, inflammation control agent, and as a nutritional adjunctive therapy in the treatment of inflammatory disorders such as arthritis, allergies, and/or immune system disorders. It has also been suggested that DDA may have potential in reducing pain and inflammation related to cardiovascular disease. There is, however, no readily available rich source for this fatty acid known in nature. It is not produced by standard oilseed crops such as *Brassica* or *Camelina*, nor has it been reported as a component of presently available edible oil products.

Docosatrienoic acid (22:3-13,16,19), referred to herein as DTA, is an omega-3 fatty acid which is 22 carbons in length and has 3 cis double bonds at positions 13, 16, and 19. DTA may have similar pharmaceutical properties to DDA due to its similar structure, with the addition of only one double bond. There is no known natural source for this fatty acid.

*Eranthis* hyemahs (winter aconite), a small tuberous perennial herb plant in the family of Ranunculaceae, can produce DDA in the bulb and seed (Aitzetmuller et al., 1996, Lipids, 31(2):201-205) although the biosynthetic mechanism of this fatty acid remains unknown. However, due to low yield, low oil content, and poorly-adaptable agronomic nature, this wild plant species has not been suitable for agricultural production of this fatty acid. Winter aconite does not produce DTA.

Long chain PUFAs and VLCFAs, in general, appear to have important biological functions. Long chain PUFAs are often found in biological tissues, including the brain, eyes and spermatozoa of animals, including humans. VLCFAs are found as constituents of cellular lipids, such as sphingolipids and glycerophospholipids, but are also precursors of important lipid mediators that have a wide range of biological functions. A variety of inherited diseases, such as ichthyosis, macular degeneration, myopathy, mental retardation, and demyelination, are caused by defects in the genes responsible for making VLCFA. The ability to make and supplement very long chain fatty acids may, therefore, provide an opportunity to treat disease. PUFAs such as 24:6n-3, 24:5n-3 and 24:5n-6, in addition to longer PUFAs, are important components of tissues such as the retina, while monounsaturated VLCFA make up large components of sphingomyelin of the nervous system. The biological importance of these fatty acids is just beginning to be understood, but they may have considerable potential as supplements and therapeutic agents.

Accordingly, there is a desire for alternative, additional, and/or improved long and very long chain unsaturated fatty acid products and/or methods for production thereof.

SUMMARY OF INVENTION

Provided are various embodiments related to an elongase enzyme, nucleic acid molecules encoding the enzyme, and applications of the enzyme and nucleic acid molecules, optionally in combination with a second elongase enzyme or a nucleic acid molecule encoding the second elongase enzyme, to produce long chain and very long chain unsaturated and polyunsaturated fatty acids.

A first embodiment is an isolated nucleic acid molecule encoding an elongase enzyme, said nucleic acid molecule comprising: a nucleotide sequence having at least 70% sequence identity to the nucleotide sequence set forth in SEQ ID NO: 5; a codon degenerate nucleotide sequence of SEQ ID NO: 5; a nucleotide sequence as set forth in SEQ ID NO: 6; a nucleotide sequence encoding a polypeptide having at least 85% sequence identity to the amino acid sequence set forth in SEQ ID NO: 4; or a nucleotide sequence encoding a polypeptide having a conservatively substituted amino acid sequence of SEQ ID NO: 4. In a further embodiment, the nucleic acid molecule comprises a nucleotide sequence having at least 85% or at least 95% sequence identity to the nucleotide sequence set forth in SEQ ID NO: 5. In an embodiment, the nucleic acid molecule comprises SEQ ID NO: 5. In another embodiment the nucleic acid molecule comprises a nucleotide sequence having at least 90% or at least 95% sequence identity to the amino acid sequence set forth in SEQ ID NO: 4. In yet another embodiment, the nucleic acid molecule encodes a polypeptide comprising the amino acid sequence set forth in SEQ ID NO: 4.

Another embodiment is an isolated elongase enzyme comprising an amino acid sequence having at least 85% sequence identity to the amino acid sequence set forth in SEQ ID NO: 4, comprising a conservatively substituted amino acid sequence of SEQ ID NO: 4, or comprising an amino acid sequence encoded by the nucleic acid molecule described above. In a further embodiment, the isolated elongase enzyme comprises an amino acid sequence having at least 90% or at least 95% sequence identity to the amino acid sequence set forth in SEQ ID NO: 4. In another embodiment the isolated elongase enzyme comprises the amino acid sequence set forth in SEQ ID NO: 4. In yet another embodiment, the isolated elongase enzyme consists of the amino acid sequence set forth in SEQ ID NO: 4.

A further embodiment is an expression vector, phage, or plasmid comprising a nucleic acid molecule as described above. In an additional embodiment, the expression vector, phage, or plasmid, further comprises a second nucleic acid molecule encoding a second elongase enzyme, wherein the second elongase enzyme encoded by the second nucleic acid molecule: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

A still further embodiment is a transgenic organism comprising a nucleic acid molecule as described above. In an embodiment the transgenic organism further comprises a second nucleic acid molecule encoding a second elongase enzyme, as described above. wherein the second elongase enzyme encoded by the second nucleic acid molecule: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

In an embodiment, the transgenic organism is a plant. In a further embodiment, the plant is an oilseed plant. In an embodiment, the plant is *Brassica napus, Brassica juncea, Brassica carinata, Brassica oleracea, Brassica nigra, Brassica rapa, Sinapis alb, Camelina sativa*, borage (*Borago* sp.) flax (*Linum* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), or peanut (*Arachis* sp.). In yet another embodiment, the plant is *Camelina sativa* or *Brassica carinata.*

In an embodiment, the transgenic organism is a microbe. In an embodiment, the microbe is a yeast, fungus, bacterium, or alga. In a further embodiment, the microbe is a yeast which is *Yarrowia lipolytica, Endomyces vernalis, Rhodotorula gracilis, Rhodotorula glutinis, Rhodotorula graminis, Rhodosporidium toruloides, Lipomyces starkeyi, Lipomyecs lipofer, Saccharomyces cerevisiae*, or *Trichosporon oleaginous*. In another embodiment the microbe is a fungus which is *Thaustochytrium* sp., *Schizochytrium* sp., *Japonochytrium* sp., *Labyrinthula* sp., or *Ulkenia* sp. In yet another embodiment, the microbe is an alga which is *Crypthecodinium cohnii, Conyaulax catenella, Conyaulax polyedra, Gyrodinium simplex, Gyrodinium cohnii, Isochysis galbana, Pavlova lutheri, Amphidinium carteri, Cryptomonas ovata, Gymnodinium nelsoni, Prorocentrum cordatum, Thalassiosira pseudonana*, or *Phaeodactylum tricornutum.*

Another embodiment is a genetically modified seed comprising a nucleic acid molecule as described above. In an embodiment, the genetically modified seed is a *Brassica napus, Brassica juncea, Brassica carinata, Brassica oleracea, Brassica nigra, Brassica rapa, Sinapis alb, Camelina sativa*, borage (*Borago* sp.) flax (*Linum* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), or peanut (*Arachis* sp.) seed. In a further embodiment, the genetically modified seed is a *Camelina sativa* or *Brassica carinata* seed. In a still further embodiment, the seed comprises a second nucleic acid molecule encoding a second elongase enzyme, wherein the second elongase enzyme encoded by the second nucleic acid molecule: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

Yet another embodiment is a genetically modified cell comprising a nucleic acid molecule as described above. In an embodiment, the genetically modified cell is a *Brassica napus, Brassica juncea, Brassica carinata, Brassica oleracea, Brassica nigra, Brassica rapa, Sinapis* alb, *Camelina sativa*, borage (*Borago* sp.) flax (*Linum* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), or peanut (*Arachis* sp.) cell. In a further embodiment, the genetically modified cell is a *Camelina sativa* or *Brassica carinata* cell. In a still further embodiment, the cell comprises a second nucleic acid molecule encoding a second elongase enzyme, wherein the second elongase enzyme encoded by the second nucleic acid molecule: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

A further embodiment is a method for producing at least one unsaturated fatty acid comprising 20 or more carbons, said method comprising: providing a transgenic organism comprising a nucleic acid molecule as described above; expressing the nucleic acid molecule in the transgenic organism; and allowing the transgenic organism to produce the at least one unsaturated fatty acid. In an embodiment, the at least one unsaturated fatty acid produced by the method is a C20, C22, or C24 unsaturated fatty acid. In another embodiment, the at least one unsaturated fatty acid produced by the method is 20:1-11 fatty acid; 20:1-13 fatty acid; 22:1-13 fatty acid; 22:1-15 fatty acid; 24:1-17 fatty acid; 26:1-19 fatty acid; 20:2-11,14 fatty acid; 22:2-13,16 fatty acid; 24:2-15,18 fatty acid; 20:3-11,14,17 fatty acid; 22:3-

13,16,19 fatty acid; 24:3-15,18,21 fatty acid; 20:3-8,11,14 fatty acid; 22:3-10,13,16 fatty acid; 20:4-8,11,14,17 fatty acid; 22:4-10,13,16,19 fatty acid; 24:4-12,15,18,21 fatty acid; 22:4-7,10,13,16 fatty acid; 24:4-9,12,15,18 fatty acid; 22:5-7,10,13,16,19 fatty acid; 24:5-9,12,15,18,21 fatty acid; 24:6-6,9,12,15,18,21 fatty acid; or a combination of two or more thereof. In a further embodiment, the at least one unsaturated fatty acid produced by the method is docosadienoic acid (DDA), docosatrienoic acid (DTA), or a combination of both DDA and DTA.

In some embodiments of the method, the transgenic organism is provided with a feedstock comprising an EhELO1 substrate fatty acid, or a precursor thereof. In an embodiment, the feedstock comprises 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof. In another embodiment, the feedstock comprises 20:2-11,14 fatty acid or 20:3-11,14,17 fatty acid.

In an embodiment, the method further comprises a step of purifying one or more unsaturated fatty acids of the at least one unsaturated fatty acid from the transgenic organism or a tissue or part thereof.

In an embodiment, the transgenic organism used in the method is an oilseed plant. In a further embodiment, the oilseed plant is *Brassica napus, Brassica juncea, Brassica carinata, Brassica oleracea, Brassica nigra, Brassica rapa, Sinapis* alb, *Camelina sativa*, borage (*Borago* sp.) flax (*Linum* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), or peanut (*Arachis* sp.). In another embodiment, the oilseed plant is *Camelina sativa* or *Brassica carinata.*

In an embodiment, the transgenic organism used in the method is a microbe. In an embodiment, the microbe is a yeast, fungus, bacterium, or alga. In a further embodiment, the microbe is a yeast which is *Yarrowia lipolytica, Endomyces vernalis, Rhodotorula gracilis, Rhodotorula glutinis, Rhodotorula graminis, Rhodosporidium toruloides, Lipomyces starkeyi, Lipomyecs lipofer, Saccharomyces cerevisiae*, or *Trichosporon oleaginous*. In another embodiment, the microbe is a fungus which is *Thaustochytrium* sp., *Schizochytrium* sp., *Japonochytrium* sp., *Labyrinthula* sp., or *Ulkenia* sp. In yet another embodiment, the microbe is an alga which is *Crypthecodinium cohnii, Conyaulax catenella, Conyaulax polyedra, Gyrodinium simplex, Gyrodinium cohnii, Isochysis galbana, Pavlova lutheri, Amphidinium carteri, Cryptomonas ovata, Gymnodinium nelsoni, Prorocentrum cordatum, Thalassiosira pseudonana*, or *Phaeodactylum tricornutum*. In a still further embodiment, the transgenic organism is an oleaginous transgenic organism that produces 20:2-11,14 fatty acid, 20:3-11,14,17 fatty acid, 18:2-9,12 fatty acid, 18:3-9,12,15 fatty acid, or a combination of one or more thereof.

In a further embodiment of the method, the transgenic organism expresses a second elongase enzyme that produces 20:2-11,14 fatty acid, 20:3-11,14,17 fatty acid, or both. In an embodiment, the second elongase enzyme: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

Yet another embodiment is an ex vivo method for producing at least one unsaturated fatty acid comprising 20 or more carbons from a substrate feedstock, the method comprising: providing the substrate feedstock, said substrate feedstock comprising an EhELO1 substrate fatty acid; exposing the substrate feedstock to an elongase enzyme as described herein; and allowing the elongase enzyme to produce the at least one unsaturated fatty acid.

In an embodiment of the ex vivo method, the substrate feedstock comprises 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof. In a further embodiment, the feedstock comprises 20:2-11,14 fatty acid or 20:3-11,14,17 fatty acid. In a still further embodiment, the ex vivo method comprises a purification step to purify one or more unsaturated fatty acids of the at least one unsaturated fatty acid produced by the method.

In another embodiment of the ex vivo method, a second elongase enzyme that produces 20:2-11,14 fatty acid, 20:3-11,14,17 fatty acid, or both, is used to enrich the substrate feedstock with 20:2-11,14 fatty acid, 20:3-11,14,17 fatty acid, or both. In an embodiment, the second elongase enzyme: is *Conidiobolus thromboides* elongase CtELO6, or a functional variant thereof; is encoded by a nucleic acid molecule having at least 95% sequence identity to the nucleotide sequence set forth in SEQ ID NO:7; is encoded by a nucleic acid molecule having a codon degenerate nucleotide sequence of SEQ ID NO:7; comprises an amino acid sequence having at least 95% sequence identity to the amino acid sequence encoded by SEQ ID NO: 7; or comprises a conservatively substituted amino acid sequence of the amino acid sequence encoded by SEQ ID NO: 7.

Yet another embodiment is the use of a nucleic acid molecule as described above for producing an unsaturated fatty acid comprising 20 or more carbons. In an embodiment, the unsaturated fatty acid is a C20, C22, or C24 unsaturated fatty acid. In an embodiment, the nucleic acid molecule is used to produce 20:1-11 fatty acid; 20:1-13 fatty acid; 22:1-13 fatty acid; 22:1-15 fatty acid; 24:1-17 fatty acid; 26:1-19 fatty acid; 20:2-11,14 fatty acid; 22:2-13,16 fatty acid; 24:2-15,18 fatty acid; 20:3-11,14,17 fatty acid; 22:3-13,16,19 fatty acid; 24:3-15,18,21 fatty acid; 20:3-8,11,14 fatty acid; 22:3-10,13,16 fatty acid; 20:4-8,11,14,17 fatty acid; 22:4-10,13,16,19 fatty acid; 24:4-12,15,18,21 fatty acid; 22:4-7,10,13,16 fatty acid; 24:4-9,12,15,18 fatty acid; 22:5-7,10,13,16,19 fatty acid; 24:5-9,12,15,18,21 fatty acid; 24:6-6,9,12,15,18,21 fatty acid; or a combination of two or more thereof. In a further embodiment, the nucleic acid molecule is used to produce docosadienoic acid (DDA), docosatrienoic acid (DTA), or a combination of both DDA and DTA.

Another embodiment is an oil product produced by a transgenic organism as described above, said oil product comprising docosadienoic acid (DDA), docosatrienoic acid (DTA), or a mixture thereof. In an embodiment, the oil product is produced by a transgenic plant as described above. In another embodiment, the oil product is produced by a method or ex vivo method as described above.

BRIEF DESCRIPTION OF DRAWINGS AND LISTING OF SEQUENCES

Features, aspects and advantages of the present invention will become better understood with regard to the following description and accompanying drawings wherein.

Figure 1:
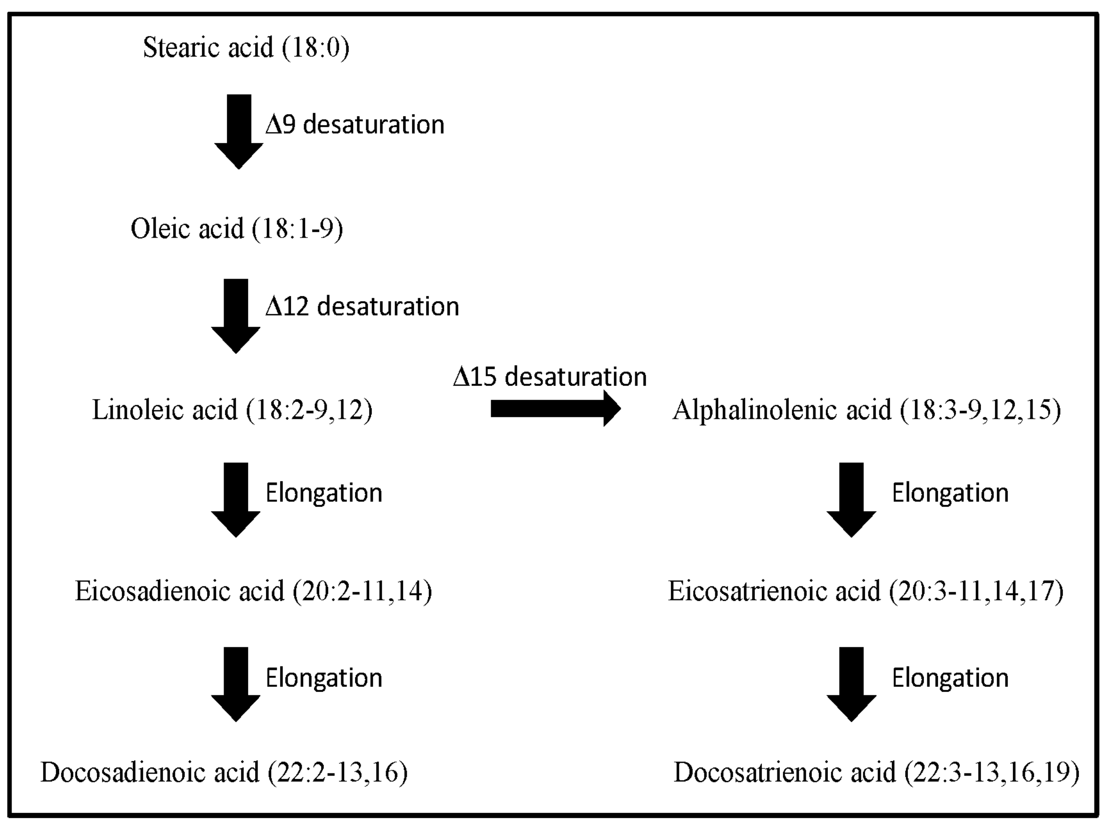
FIG. 1 shows a hypothesized potential biosynthesis pathway of DDA in *E. hyemalis;*

The following is a list of sequences appearing in the document:

SEQ ID NO: 1 is a primer having the sequence:

```
TCTAGAATGGAGTCCATTTCTGCTAG
```

SEQ ID NO: 2 is a primer having the sequence:

```
TCTAGATTAAACCAGCTTCTTATCCTTG
```

SEQ ID NO: 3 is the full length cDNA of *E. hyemalis* EhELO1

```
atgcttccttcatttgtttcaaaaATGGAGTCCATTTCTGCTAGTGTACG
CTACTGGCTAGTAGAACACCCATTGGTGAGCGGATTCGAGTGGATAGAAG
```

-continued

```
GCGAAACATTTGGTTCATCGCCAAAATTTCTTCTAACCACGGTAGCCACC
TACCTCTCCCTAACCTACATCCTCTCCATCACCCTTCTTTCACCGAAACC
TCCAGTGAAAACCCCCTCCAAGACCCTTACCATCCTCCGGTCTATCTCCG
CAATACATAACCTGATTCTCCTTGCCCTCTCCTTCATAATGGCCTTGGGA
GCGACATTAGCAACCACCACCAAAATGCCAAGCAAGCAATGGATCTGTTT
CCCAGCAAACAAAACCCGATCACAGGGTCCACTATTTTTCTGGGCTTATG
TGTTCTACCTATCCAAGATACTTGAATACGTAGATACCCTCTTGATCATC
CTCCACAACGACGCAAGGAGACTCACATTTCTCCATGTCTACCATCACAC
TGTTGTTACTATCATGTGTTACCTTTGGCTACACACTACACAATCTCTCT
TACCTTTGGGGATTGTTACCAATGCCACCGTGCATACTGTCATGTATGCT
TATTATTTCATGTGCACACTTGGGAAAAGGCCATCTTGGAAGAGGTTAGT
GACAGATTTCCAGATCATTCAGTTTTGGTTTGGTCTCGGGATCTCCACGT
TGATGTTGTGGTTCCATTTTACTGGAACTGGCTGCTCTGGGATTTGGGGA
TGGGGTTTTTCTTATGTCTTCAATGCTTCTCTTCTTGCTCTATTTAGTGC
TTTTCATGCTAACAACTACGCCAACAAGGACAAGGATAAGAAGCTGGTTT
AActgcctatttatggggtctattcgtgtggctatatcaccatcccacgc
gatcagaatctatttaggatatccttgtatcaataagttaagtttgttt
```

SEQ ID NO: 4 is the amino acid sequence of the EhELO1 fatty acid elongase polypeptide:

```
MESISASVRYWLVEHPLVSGFEWIEGETFGSSPKFLLTTVATYLSLTYIL
SITLLSPKPPVKTPSKTLTILRSISAIHNLILLALSFIMALGATLATTTK
MPSKQWICFPANKTRSQGPLFFWAYVFYLSKILEYVDTLLIILHNDARRL
TFLHVYHHTVVTIMCYLWLHTTQSLLPLGIVTNATVHTVMYAYYFMCTLG
KRPSWKRLVTDFQIIQFWFGLGISTLMLWFHFTGTGCSGIWGWGFSYVFN
ASLLALFSAFHANNYANKDKDKKLV
```

SEQ ID NO: 5 is the coding sequence of the cDNA sequence of EhELO1 fatty acid elongase gene:

```
ATGGAGTCCATTTCTGCTAGTGTACGCTACTGGCTAGTAGAACACCCATT
GGTGAGCGGATTCGAGTGGATAGAAGGCGAAACATTTGGTTCATCGCCAA
AATTTCTTCTAACCACGGTAGCCACCTACCTCTCCCTAACCTACATCCTC
TCCATCACCCTTCTTTCACCGAAACCTCCAGTGAAAACCCCCTCCAAGAC
CCTTACCATCCTCCGGTCTATCTCCGCAATACATAACCTGATTCTCCTTG
CCCTCTCCTTCATAATGGCCTTGGGAGCGACATTAGCAACCACCACCAAA
ATGCCAAGCAAGCAATGGATCTGTTTCCCAGCAAACAAAACCCGATCACA
GGGTCCACTATTTTTCTGGGCTTATGTGTTCTACCTATCCAAGATACTTG
AATACGTAGATACCCTCTTGATCATCCTCCACAACGACGCAAGGAGACTC
ACATTTCTCCATGTCTACCATCACACTGTTGTTACTATCATGTGTTACCT
TTGGCTACACACTACACAATCTCTCTTACCTTTGGGGATTGTTACCAATG
CCACCGTGCATACTGTCATGTATGCTTATTATTTCATGTGCACACTTGGG
AAAAGGCCATCTTGGAAGAGGTTAGTGACAGATTTCCAGATCATTCAGTT
```

-continued

```
TTGGTTTGGTCTCGGGATCTCCACGTTGATGTTGTGGTTCCATTTTACTG
GAACTGGCTGCTCTGGGATTTGGGGATGGGGTTTTTCTTATGTCTTCAAT
GCTTCTCTTCTTGCTCTATTTAGTGCTTTTCATGCTAACAACTACGCCAA
CAAGGACAAGGATAAGAAGCTGGTTTAA
```

SEQ ID NO: 6 is a codon optimized coding sequence of the cDNA sequence of EhELO1 fatty acid elongase gene, where codon optimization was conducted according to codon usage in *Brassica*:

```
ATGGAGTCCATCTCTGCAAGCGTCCGTTATTGGCTTGTAGAGCACCCACT
TGTGTCAGGATTCGAGTGGATCGAGGGAGAGACTTTTGGTTCTTCTCCAA
AATTTTTGCTGACCACTGTGGCTACTTATCTATCGTTAACGTATATTCTG
TCCATCACTCTTCTCTCTCCTAAACCGCCTGTCAAAACACCGTCTAAGAC
TCTTACGATCTTAAGATCTATTAGCGCTATTCACAACTTGATCTTGTTGG
CTCTTAGTTTTATCATGGCACTTGGAGCAACATTGGCGACAACTACCAAG
ATGCCCAGCAAGCAATGGATCTGTTTCCCGGCTAACAAGACCAGGAGCCA
GGGTCCATTGTTCTTCTGGGCATACGTTTTTTATCTAAGTAAAATCCTGG
AATACGTCGATACCCTCCTTATAATCCTCCACAACGACGCGAGGAGACTA
ACTTTTTTGCATGTGTATCACCACACTGTGGTTACCATCATGTGTTATTT
GTGGCTTCATACTACCCAATCACTTTTGCCCTTAGGAATAGTTACAAACG
CCACAGTGCATACCGTAATGTACGCTTACTACTTCATGTGTACCCTGGGA
AAACGTCCATCTTGGAAGAGACTAGTCACAGATTTCCAAATTATCCAATT
CTGGTTTGGTCTCGGGATCTCGACCCTTATGCTCTGGTTTCACTTCACAG
GCACTGGTTGTAGCGGAATCTGGGGTTGGGGATTTTCATACGTCTTTAAC
GCTTCCTTGTTGGCTCTATTCAGTGCTTTCCATGCAAACAACTACGCCAA
CAAGGACAAGGATAAGAAGCTAGTCTGAT
```

SEQ ID NO: 7 is the coding region cDNA of *Conidiobolus thromboides* CtELO6

```
ATGAGTTTATTAAATACATTGGATACTATTACTTCAAGCAATAATGTTGT
ATCAGCATACAACGATGCCCCAGTAGACTATTTAATTAAAGTAGTAGATT
TAGCTTTAACTGCTAACAAAGCAGTCTTCAATGTTATAGAAGCCAAAGTT
AACGTATGGATGCCAACATTGATGATAAACTTAAGAGAACAGGTCTCTAA
TTTAATCTCACCAATAAGTAAATACTTGCCATTGTTAGATCCTATCGAAG
TGTTTTCTATCTTGTTTTTATATATCTTTGTTGTGTTTTTTTGGCTCAAA
GTAGCTTCTAGCTTCCTCCCACGTTTCGAAGTAAGATTATTTTCCCTTTT
CCATAATTTCTGTATGGTCGTTTTATCCGCCTATATGTGCTCTTCCATCC
TATTACAAGCTTATGCAGATAAGTATATTCTATTCACTAACCCCGTCGAT
CACTCTCCAAATGGTATTCCAATGGCTAAAATAATATGGTTATTTTATAT
TTCCAAAATCCCAGAGTTCGTTGACACTATGATCATGTTGGTTAAACAAA
ACTACCGCCAAATCTCCTTTTTACATGTCTACCATCATAGTTCGATCTTT
GCTATTTGGTGGATTGTTACCTTGATGGCACCAAATGGTGATGCTTATTT
```

-continued

```
CTCAGCTGCATTGAACTCATTTATTCATGTTGTTATGTACGGATATTATT
TACTCTCTGCACTTGGATTCAAATCCGTCTCCTTTGTTAAGAAATATATT
ACTATGGGACAAATGACTCAATTTGCACTCAACTTTGTTCAAGCTAGTTA
TAATATTGTAGACAGAAATTACTTACGTCCACAAGTCCATGAGCAAGGAT
TAGCCTATCCTTATGCTCTTTCCGTTTTACTTTGGTTCTATATGATCTCT
ATGTTGGTGTTATTCGCTAACTTTTATATTCAAGATCGTATCCGTCAATC
AAAGTTAAAGTCTCAACAAAAGGGAAAGAAAATGAATTAG
```

DETAILED DESCRIPTION

The following description is of particular embodiments by way of example only, and is intended for the person of skill in the art. Examples and embodiments herein are intended as non-limiting examples and embodiments.

Described herein are long and very long chain fatty acids, and methods for the production thereof. Fatty acid chains differ in length and can be characterized by the number of carbons in the aliphatic tail. As used herein, "long chain" fatty acids have an aliphatic tail with 13 to 21 carbons and "very long chain" fatty acids have an aliphatic tail with 22 or more carbons.

Fatty acids can further be characterized as saturated or unsaturated. Saturated fatty acids do not contain any double-bonds between carbon atoms, whereas unsaturated fatty acids have one or more double bonds between carbon atoms. As used herein the term "unsaturated fatty acid" is intended to include any fatty acid comprising one or more double bonds within the fatty acid chain. For greater clarity, as used herein "unsaturated fatty acid" includes both monounsaturated fatty acids, fatty acids comprising only one double bond within the fatty acid chain, and polyunsaturated fatty acids, fatty acids comprising two or more double bonds within the fatty acid chain.

Fatty acids terminate in a carboxyl (COOH) group at one end (the alpha end) and a methyl ($CH_3$) group at the opposite end (the omega end). The position of carbon atoms within a fatty acid is counted either from the carboxyl end or the methyl end of the fatty acid, with the carbon of the COOH or $CH_3$ group indicated as position 1. When the carbon position is provided from the CH3 end, it is provided using n-x, ω-x, or omega-x nomenclature. For example, an omega-3 fatty acid includes a double bond after the third carbon, counting from the CH3 terminus of the fatty acid.

There are several systems for naming fatty acids, including common names, also known as trivial names, such as docosadienoic acid (DDA); systematic names (or IUPAC names); $\Delta^x$ nomenclature, where each double bond is indicated by $\Delta^x$ preceded by cis or trans; n-x nomenclature, also seen as ω-x, or omega-x, as discussed above; and by lipid numbers taking the form of C:D-x, where C is the number of carbon atoms, D is the number of double bonds, and x indicates the position(s) of the double bond(s), as counted from the carboxyl end of the fatty acid. For example, 22:2-13,16 denotes a fatty acid with 22 carbons and 2 double bonds, with the double bonds located between the $13^{th}$ and $14^{th}$ carbons and between the $16^{th}$ and $17^{th}$ carbons, as counted starting from the COOH end of the fatty acid.

Provided are unsaturated long chain and very long chain fatty acids, such as DDA and DTA, as well as transgenic organisms, plants, seeds, cells, expression vectors, phages, plasmids, nucleic acids, and enzymes relating to the production thereof. Nutraceutical and functional food products, pharmaceuticals, supplements, cosmetics, and/or personal care industry products comprising these fatty acids are also contemplated.

The structure of DDA is provided in Formula (I) below.

(I)

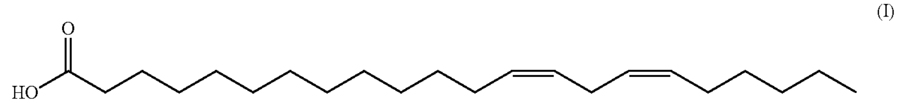 [SMILES: CCCCC/C=C\C/C=C\CCCCCCCCCCCC(=O)O]

The structure of DTA is provided in Formula (IV) below.

(IV)

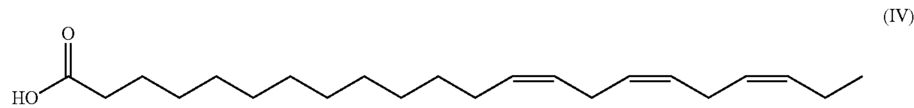 [SMILES: CC/C=C\C/C=C\C/C=C\CCCCCCCCCCCC(=O)O]

Due to the amount of DDA observed in the mature seeds of *Eranthis hyemalis*, the present inventors hypothesized that DDA biosynthesis may be occurring in developing seeds, and thus genes and enzymes involved in the biosynthesis of DDA may likely be highly expressed during seed development. Without wishing to be bound by theory, a potential pathway for DDA biosynthesis hypothesized by the inventors is shown in FIG. 1. There are generally two types of condensing enzymes which are responsible for the elongation of fatty acids by adding a two carbon unit to the carboxyl end of a fatty acid. The first belongs to ketoacyl-CoA synthases (KCSs) (also known as fatty acid elongation 1, FAE1-type), and the other belongs to elongation defective-like elongase (ELO-type). The potential pathway involves two elongation steps starting from linoleic acid (18:2-9,12) as indicated by "elongation" steps in FIG. 1. The inventors have theorized that one of these types of enzymes could play a role in catalyzing the shown elongation. No previous publication is believed to have reported on an identification of this polyunsaturated fatty acid (PUFA) elongation step in land plants. Based on the hypothesized potential pathway, the condensing enzymes may be rate limiting, and may provide substrate specificity in the elongation step involved in the pathway.

The inventors hypothesized herein that total RNA isolation and analysis from seeds, using techniques such as degenerate RT-PCR cloning and/or EST sequencing and homology searching, might allow for the identification of previously unknown genes involved in DDA synthesis. It was proposed that RT-PCR techniques involving degenerate primers targeting conserved domains of selected elongases and related sequences from other species may be used to amplify a portion of an unknown gene, potentially allowing its identity to be determined by sequencing. If an amino acid sequence encoded by an identified partial cDNA was homologous to a predicted enzyme, then RACE approaches may be adopted to retrieve the full length sequence of the gene. Alternative approaches were also contemplated, such as an approach involving sequencing of a random set of about 500,000 cDNA fragments derived from transcripts of the developing seeds, and use of a variety of homology search tools to identify candidate sequences homologous to elongases from other species.

As a result of experiments described further herein, a candidate winter aconite gene was identified as potentially being involved in DDA biosynthesis. This gene was termed "EhELO1" (the full-length cDNA sequence of which is provided in SEQ ID NO: 3 and the coding portion of the cDNA of which is provided in SEQ ID NO:5). To potentially obtain insights on the function, activity level, and/or substrate specificity of the enzyme encoded by the candidate gene, yeast-based functional studies were performed by cloning the gene and using it to transform the yeast *Saccharomyces cerevisiae*. As the yeast host system does not generate eicosadienoic acid (20:2-11,14, EDA) fatty acid substrate, this fatty acid substrate was supplied to the yeast. Analysis of fatty acid products obtained from yeast transformants expressing the candidate gene confirmed that those transformants expressing EhELO1 were producing DDA, flagging this gene as being involved in DDA production. These results confirm that EhELO1 isolated from *E. hyemalis* encodes a functional elongase responsible for the addition of a two carbon unit to the carboxyl end of EDA, producing DDA.

Functional expression studies on the EhELO1 gene were then performed in plants to further investigate production of DDA, DTA, and other fatty acids. Winter aconite EhELO1 was functionally expressed in *Camelina, Arabidopsis*, and *Brassica carinata*. Production of DDA, or both DDA and DTA, was successfully observed.

In order to provide more 20:2-11,14 fatty acid substrate for conversion to DDA by winter aconite EhELO1 elongase, it was further proposed that in certain applications the EhELO1 elongase could be used alongside an elongase from *Conidiobolus thromboides* (CtELO6) which produces 20:2-11,14 fatty acid, the substrate for DDA biosynthesis. A plant expression plasmid was produced for providing both EhELO1 elongase and CtELO6 elongase.

The elongase gene from winter aconite (*Eranthis hyemalis*) (EhELO1) has been found herein to be involved in the biosynthesis of DDA and DTA as well as other unsaturated fatty acids comprising 20 or more carbons, for example C20, C22 and C24 unsaturated fatty acids. Results described herein indicate that this gene may be used to produce unsaturated fatty acids comprising 20 or more carbons in transgenic organisms including plants and/or microbes. Such fatty acid production may provide unsaturated fatty acids such as DDA and/or DTA for use in nutraceuticals, functional foods, pharmaceuticals, supplements, cosmetics, and/or personal care industry products and markets, for example.

Substrate fatty acids that can be elongated by EhELO1 are herein referred to as "EhELO1 substrate fatty acids" and include, for example, the following: 18:1-9 fatty acid; 18:1-11 fatty acid; 18:2-9,12 fatty acid; 18:3-9,12,15 fatty acid; 18:3-6,9,12 fatty acid; 18:4-6,9,12,15 fatty acid; 20:1-11 fatty acid; 20:2-11,14 fatty acid; 20:3-8,11,14 fatty acid;

20:3-11,14,17 fatty acid; 20:4-5,8,11,14 fatty acid; 20:4-8,11,14,17 fatty acid; 20: 5-5,8,11,14,17 fatty acid; 22:4-7,10,13,16 fatty acid; 22:4-10,13,16,19 fatty acid; 22:5-7,10,13,16,19 fatty acid; and 22:6-4,7,10,13,16,19 fatty acid.

In an embodiment, there is provided herein a nucleic acid molecule encoding an elongase enzyme, said nucleic acid molecule comprising: a nucleotide sequence having at least 70% sequence identity to the nucleotide sequence set forth in SEQ ID NO: 5; a codon degenerate nucleotide sequence of SEQ ID NO: 5; a nucleotide sequence as set forth in SEQ ID NO: 6; a nucleotide sequence encoding a polypeptide having at least 85% sequence identity to the amino acid sequence set forth in SEQ ID NO: 4; or a nucleotide sequence encoding a polypeptide having a conservatively substituted amino acid sequence of SEQ ID NO: 4.

There is further provided herein an isolated elongase enzyme comprising an amino acid sequence having at least 85% sequence identity to the amino acid sequence set forth in SEQ ID NO: 4, comprising a conservatively substituted amino acid sequence of SEQ ID NO: 4, or comprising an amino acid sequence encoded by the nucleic acid molecule described above.

Additionally provided is a method for producing at least one unsaturated fatty acid comprising 20 or more carbons, said method comprising: providing a transgenic organism comprising a nucleic acid molecule as described herein; expressing the nucleic acid molecule in the transgenic organism; and allowing the transgenic organism to produce the at least one unsaturated fatty acid. The at least one unsaturated fatty acid produced by the method may be a C20, C22, or C24 unsaturated fatty acid. By way of example, the at least one unsaturated fatty acid may be 20:1-11 fatty acid; 20:1-13 fatty acid; 22:1-13 fatty acid; 22:1-15 fatty acid; 24:1-17 fatty acid; 26:1-19 fatty acid; 20:2-11,14 fatty acid; 22:2-13,16 fatty acid; 24:2-15,18 fatty acid; 20:3-11,14,17 fatty acid; 22:3-13,16,19 fatty acid; 24:3-15,18,21 fatty acid; 20:3-8,11,14 fatty acid; 22:3-10,13,16 fatty acid; 20:4-8,11,14,17 fatty acid; 22:4-10,13,16,19 fatty acid; 24:4-12,15,18,21 fatty acid; 22:4-7,10,13,16 fatty acid; 24:4-9,12,15,18 fatty acid; 22:5-7,10,13,16,19 fatty acid; 24:5-9,12,15,18,21 fatty acid; 24:6-6,9,12,15,18,21 fatty acid; or a combination of two or more thereof. The at least one unsaturated fatty acid may be docosadienoic acid (DDA), docosatrienoic acid (DTA), or a combination of both DDA and DTA.

In embodiments where the transgenic organism does not produce fatty acid substrate for the elongase enzyme, or does not produce such substrate in sufficient quantities, the transgenic organism may be provided with a feedstock comprising an EhELO1 substrate fatty acid, or a precursor thereof. By way of example, the EhELO1 substrate fatty acid may comprise 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof. To encourage production of DDA or DTA, respectively, the feedstock may comprise 20:2-11,14 fatty acid, or a precursor thereof, or 20:3-11,14,17 fatty acid, or a precursor thereof.

In certain embodiments, the substrate feedstock may be chosen so as to encourage production of one fatty acid over another by the transgenic organism; for example, DDA over DTA, or vice versa. For example, a feedstock enriched in 20:2-11,14 fatty acid and/or 18:2-9,12 fatty acid may favor DDA production, whereas a feedstock enriched in 20:3-11,14,17 fatty acid and/or 18:3-9,12,15 fatty acid may favor DTA production. The structures of 20:2-11,14; 20:3-11,14,17; 18:2-9,12; and 18:3-9,12,15 EhELO1 substrate fatty acids are provided below as Formulas (II), (V), (III), and (VI), respectively.

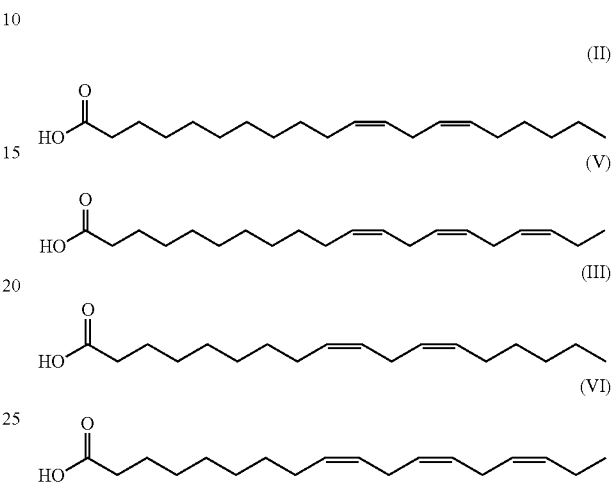

It will be understood by those of skill in the art that the elongase enzyme or variant thereof, may be used ex vivo as a chemical catalyst, effecting conversion of the substrate fatty acid feedstock into an unsaturated fatty acid comprising 20 or more carbons; optionally 20, 22, or 24 carbons. In certain embodiments, the substrate feedstock may comprise 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof. In other embodiments, the feedstock may comprise 20:2-11,14 fatty acid and/or 20:3-11,14,17 fatty acid. When DDA and/or DTA production is desired, and where the feedstock comprises insufficient 20:2-11,14 fatty acid and/or 20:3-11,14,17 fatty acid, an elongase which produces 20:2-11,14 fatty acid, 20:3-11,14,17 fatty acid, or both, may additionally be used to enrich the feedstock with said fatty acid(s). Such an elongase may be, for example, *Conidiobolus thromboides* elongase CtELO6, or a variant thereof. As well, certain of these embodiments may further comprise an optional purification step, where the at least one produced fatty acid, for example DDA, DTA, or both is purified to provide an isolated fatty acid or fatty acid mixture sample, for example an isolated DDA sample, an isolated DTA sample, or an isolated DDA and DTA mixture sample. Such a purification step may be desirable depending on the feedstock used.

As used herein, an "isolated" fatty acid or fatty acid mixture that is "purified" from a starting material refers to a sample that is substantially enriched for the produced fatty acid or fatty acid mixture, relative to the starting material from which the isolated fatty acid or fatty acid mixture is purified. An enrichment may be considered substantial if the proportion of fatty acid or fatty acid mixture in the sample, relative to the total fatty acid population in the sample, is increased by at least 50%. It is not required that the isolated fatty acid sample be a pure sample, or that the purification step remove all contaminants in order for the fatty acid or fatty acid mixture to be considered isolated or purified. For example, an isolated fatty acid or fatty acid mixture may have a purity of 90% or higher for the produced fatty acid or fatty acid mixture.

Accordingly, there is provided another embodiment which is an ex vivo method for producing at least one unsaturated fatty acid comprising 20 or more carbons from a substrate feedstock, the method comprising: providing the substrate feedstock, said substrate feedstock comprising an EhELO1 substrate fatty acid; exposing the substrate feedstock to an elongase enzyme as described herein; and allowing the elongase enzyme to produce the at least one unsaturated fatty acid.

Alternatively, a whole oil product produced by a method as described herein, for example but not limited to an ex vivo method as described herein, may be further purified to obtain enriched or pure DDA, DTA, or a mixture thereof, according to the particular application contemplated.

As a further embodiment, there is provided a transgenic organism, which has been modified to produce at least one unsaturated fatty acid comprising 20 or more carbons. The transgenic organism may be a genetically modified seed, cell, transgenic plant, plant seed, or plant cell comprising a nucleic acid molecule encoding an elongase enzyme, as described herein. The transgenic organism of the invention may optionally further comprise a *Conidiobolus thromboides* elongase CtELO6 gene, or a variant thereof.

As will be understood, a transgenic organism as referred to herein may be any suitable organism which may be genetically modified for heterologous gene expression. Organisms suitable for use as transgenic organisms may include single or multicellular organisms. Examples of suitable organisms may include plant cells, plants, and microbes/microorganisms, for example. Indeed, organisms suitable for use as transgenic organisms may include various types of plants, fungi, bacteria, and/or algae.

In certain embodiments, a transgenic organism as referred to herein may be a plant, such as an oilseed plant, which is genetically modified to express an elongase as described herein, or a functional equivalent thereof. In certain embodiments, the transgenic organism may be a genetically modified *Brassica napus, Brassica juncea, Brassica carinata, Brassica oleracea, Brassica nigra, Brassica rapa, Sinapis* alb, *Camelina sativa*, borage (*Borago* sp.) flax (*Linum* sp.), soybean (*Glycine* and *Sola* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), or peanut (*Arachis* sp.).

The inventors of the present application have observed that methods as described herein work surprisingly well to produce DDA and DTA in a variety of *B. carinata* that expresses a low level of erucic acid and a high amount of linoleic acid and/or linolenic acid. Without being bound by theory, it is possible that this variety of *B. carinata* has a pool of fatty acid precursors available for use in production of DDA and DTA. As such, it is further likely that methods as described herein may work well in varieties of *Brassica* which have been bred or altered to express low levels of erucic acid (eg. *B. juncea, B. napus*). Accordingly, in a certain preferred embodiments, the transgenic organism may be *B. carinata, B. juncea*, or *B. napus*. In a very preferred embodiment, the transgenic organism may be *B. carinata.*

In certain other embodiments, a transgenic organism as referred to herein may be a yeast that is genetically modified to express an elongase as described herein, or a functional equivalent thereof. In certain embodiments, the transgenic organism may be a genetically modified *Yarrowia hpolytica, Endomyces vernalis, Rhodotorula gracilis, Rhodotorula glutinis, Rhodotorula graminis, Rhodosporidium toruloides, Lipomyces starkeyi, Lipomyecs lipofer, Saccharomyces cerevisiae*, or *Trichosporon oleaginous*. A person of skill in the art will recognize that yeast does not produce substrate for the method, and therefore a fatty acid substrate may be added, as is further described below.

In certain other embodiments, a transgenic organism as referred to herein may be a fungus, which is genetically modified to express an elongase as described herein, or a functional equivalent thereof. In certain embodiments, the transgenic organism may be a genetically modified *Thraustochytrium* sp., *Schizochytrium* sp., *Japonochytrium* sp., *Labyrinthula* sp., or *Ulkenia* sp. A person of skill in the art will recognize that the fungus does not produce substrate for the method, and therefore a fatty acid substrate may be added, as is further described below.

In certain other embodiments, a transgenic organism as referred to herein may be an alga, which is genetically modified to express an elongase as described herein, or a functional equivalent thereof. In certain embodiments, the transgenic organism may be a genetically modified *Crypthecodinium cohnii, Conyaulax catenella, Conyaulax polyedra, Gyrodinium simplex, Gyrodinium cohnii, Isochysis galbana, Pavlova lutheri, Amphidinium carteri, Cryptomonas ovata, Gymnodinium nelsoni, Prorocentrum cordatum, Thalassiosira pseudonana*, or *Phaeodactylum tricornutum*. A person of skill in the art will recognize that the alga does not produce substrate for the method, and therefore a fatty acid substrate may be added, as is further described below.

The person of skill in the art will be aware of suitable techniques for generating transgenic organisms capable of heterologous gene expression. Indeed, suitable cloning and/or recombinant nucleic acid techniques for generating single or multicellular transgenic organisms, including animals, plants, fungi, bacteria, and/or algae single or multicellular transgenic organisms, are well-established in the field. By way of example, a vector (either viral, plasmid, or other) comprising one or more copies of the particular gene each driven by a suitable promoter sequence (for example, a constitutive or inducible promoter), may be introduced into cells via transfection, electroporation, viral infection, or another suitable method known in the art. Suitable expression vector techniques for overexpressing or introducing a particular gene into a cell are known in the art (see, for example, Molecular Cloning: A Laboratory Manual (4th Ed.), 2012, Cold Spring Harbor Laboratory Press). In plants, *Agrobacterium*-mediated plant transformation approaches, for example, may be used. The skilled person will be able to select a suitable expression vector and/or gene introduction method based on the organism to be transgenically modified.

It will be understood that gene expression may refer to the production of a polypeptide from a nucleic acid molecule. Gene expression may include both transcription and translation processes, and so gene expression may refer to production of a nucleic acid molecule such as an mRNA (i.e. transcription), production of a protein (i.e. translation), or both. Heterologous expression refers to the expression of a nucleic acid molecule in an organism which does not naturally have or express this nucleic acid molecule. It will further be understood that overexpression of a particular nucleic acid molecule in a cell may refer to increasing the expression of a particular nucleic acid molecule within a cell as compared to wild-type, baseline, or untreated levels.

Introduction of a nucleic acid molecule or gene, in the context of inserting a nucleic acid molecule into a cell, may refer to "transfection", "transformation", or "transduction", and may include the incorporation or introduction of a nucleic acid sequence into a eukaryotic or prokaryotic cell, where the nucleic acid sequence may optionally be incorporated into the genome of the cell, or transiently expressed (for example, transfected mRNA). Inserting a nucleic acid molecule into a cell produces a "genetically modified" cell. The nucleic acid molecule inserted into the cell may be referred to as an "exogenous" nucleic acid molecule; meaning a nucleic acid molecule originating from outside the cell. The exogenous nucleic acid molecule may be derived from the same species or from a different species than the organism into which it is introduced. A protein or enzyme may be introduced into a cell by delivering the protein or enzyme itself into the cell, or by expressing an mRNA encoding the protein or enzyme within the cell, leading to its translation.

As will be known to one of skill in the art, nucleotide sequences for expressing a particular gene may encode or include one or more suitable features as described in, for example, "Genes VII", Lewin, B. Oxford University Press (2000) or "Molecular Cloning: A Laboratory Manual", Sambrook et al., Cold Spring Harbor Laboratory, 3rd edition (2001). A nucleotide sequence encoding a polypeptide or protein may be incorporated into a suitable vector or expression cassette, such as a commercially available vector or expression cassette. Vectors may also be individually constructed or modified using standard molecular biology techniques, as outlined, for example, in Sambrook et al. (Cold Spring Harbor Laboratory, 3rd edition (2001)). The person of skill in the art will recognize that a vector may include nucleotide sequences encoding desired elements that may be operably linked to a nucleotide sequence encoding a polypeptide or protein. Such nucleotide sequences encoding desired elements may include suitable transcriptional promoters, transcriptional enhancers, transcriptional terminators, translational initiators, translational terminators, ribosome binding sites, 5'-untranslated region, 3'-untranslated regions, cap structure, poly-A tail, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

Results described herein indicate that the elongase identified herein may be used to produce a variety of unsaturated fatty acids comprising 20 or more carbons, including DDA and/or DTA, in transgenic organisms including oilseed plants and/or microbes. The cDNA nucleotide sequence and the amino acid sequence of the full length elongase enzyme identified herein, including 5' and 3' untranslated regions, are provided in SEQ ID NOs: 3 and 4, respectively. SEQ ID NO: 5 provides the coding sequence section of the full length cDNA nucleic acid sequence provided in SEQ ID NO: 3. SEQ ID NO: 6 provides a codon optimized coding region of the nucleic acid sequence provided in SEQ ID NO: 3, codon optimized for expression in *Brassica*. Each of SEQ ID NO: 3. SEQ ID NO: 5 and SEQ ID NO: 6 differs from the naturally occurring genomic sequence, and is included within the scope of the invention.

It will be understood that functional variants of the elongase gene may be possible and are included within the scope of the invention. A variant of the elongase gene may include any suitable nucleic acid molecule having a nucleotide sequence that varies from that of the unmodified gene, but which still encodes a protein which is functionally the same or similar to the unmodified gene product.

By way of example, it will be understood that there is degeneracy in the genetic code, and that a particular amino acid sequence may be encoded by more than one nucleotide sequence (as illustrated in Table 1 below). As such, in certain embodiments, an elongase gene variant may include any suitable nucleic acid molecule comprising a nucleotide sequence that varies from that of SEQ ID NOs: 3 or 5 or 6, but which still encodes an polypeptide having the amino acid sequence of SEQ ID NO: 4, for example a codon degenerate version of the nucleotide sequence.

In some embodiments, the codon degenerate version of the sequence may be codon-optimized according to the codon frequency of a species other than *Eranthis hyemalis*.

TABLE 1

Codon Degeneracies

| Amino Acid | Codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

By way of further example, it will be understood that in certain embodiments an elongase gene variant may also include mutant versions of the elongase gene that encode for amino acid sequences that differ from that of SEQ ID NO: 4, but which still maintain the same, or similar, functionality of the unmodified gene product. By way of example, it will be understood that one or more conservative amino acid substitutions may be possible that do not substantially affect the function of the gene product. In some embodiments, the sequence may comprise 1, up to 2, up to 3, up to 4, up to 5, up to 6, up to 7, up to 8, up to 9, up to 10, up to 15, up to 20, up to 25, up to 30, up to 35, up to 40, up to 45, up to 50, up to 55, up to 60, up to 65, up to 70, up to 75, up to 80, up to 85, up to 90, up to 95, up to 100, or more conservative amino acid substitutions. In certain embodiments, up to 5%, up to 10%, up to 15%, up to 20%, up to 25%, up to 30%, up to 35%, up to 40%, up to 45%, or up to 50% of the amino acids may be conservatively substituted.

As will be recognized, a conservative amino acid substitution may include one in which an amino acid is substituted for another amino acid having similar properties such that the folding, activity, or other functionality of the protein is not significantly affected. Examples of interchangeable aromatic amino acids, which may be substitutable, may include phenylalanine, tryptophan, and tyrosine. Examples of interchangeable hydrophobic amino acids, which may be substitutable, may include leucine, isoleucine, methionine, and valine. Examples of interchangeable polar amino acids, which may be substitutable, may include glutamine and asparagine. Examples of interchangeable basic amino acids, which may be substitutable, may include arginine, lysine and histidine. Examples of interchangeable acidic amino acids, which may be substitutable, may include aspartic acid and glutamic acid. Examples of interchangeable small amino acids, which may be substitutable, may include alanine, serine, threonine, cysteine, and glycine. Further examples of conservative amino acid substitutions are provided in Table 2. In some embodiments, the conservative substitutions may be limited to "very highly conserved" or "highly conserved" amino acid substitutions, as defined in Table 2. As used herein, the term "conservatively substituted amino acid sequence" is intended to refer to an amino acid sequence comprising one or more "conserved substitutions" as defined in the rightmost column of Table 2.

which is the same as, or similar to, that of winter aconite EhELO1 elongase (SEQ ID NO: 4).

As referenced herein, percent (%) identity or % sequence identity with respect to a particular sequence, or a specified portion thereof, may be defined as the percentage of nucleotides or amino acids in the candidate sequence that are identical with the nucleotides or amino acids in the subject sequence (or specified portion thereof), after aligning the full length of the particular sequence, or the specified portion thereof, with the subject sequence and introducing gaps, if necessary, to achieve the maximum percent sequence identity, as generated by the program WU-BLAST-2.0 with search parameters set to default values (Altschul et al., J. Mol. Biol. (1990) 215:403-410; website at blast.wustl.edu/blast/README.html).

By way of example, a % identity value may be determined by the number of matching identical nucleotides or amino acids divided by the sequence length for which the percent identity is being reported. Percent (%) amino acid sequence similarity may be determined by the same calculation as used for determining % amino acid sequence identity, but may, for example, include conservative amino acid substitutions in addition to identical amino acids in the computation. Oligonucleotide alignment algorithms such as, for example, BLAST (GenBank; using default parameters) may be used to calculate % sequence identity.

TABLE 2

Exemplary conservative amino acid substitutions

| Original Residue | Very Highly Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Other mutations, such as insertions, deletions, or substitutions, may also be possible, so long as enzyme function is not destroyed. Insertion or deletion of an amino acid residue positioned outside the enzyme active site, which does not affect overall function of the enzyme, may be an example of such a variant.

In certain embodiments, a variant of the elongase gene may comprise a nucleotide sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 99.5% sequence identity to SEQ ID NO: 3 or to SEQ ID NO: 5 or to SEQ ID NO: 6, that encodes an elongase enzyme having a functionality An alternative indication that two nucleic acid sequences may be substantially identical is that the two sequences hybridize to each other under moderately stringent, or preferably stringent, conditions. Hybridization to filter-bound sequences under moderately stringent conditions may, for example, be performed according to Ausubel, et al. (eds), 1989, Current Protocols in Molecular Biology, Vol. 1, Green Publishing Associates, Inc., and John Wiley & Sons, Inc., New York, at p. 2.10.3. Alternatively, hybridization to filter-bound sequences under stringent conditions may, for example, be performed according to Ausubel, et al. (eds), 1989, supra. Hybridization conditions may be modified in accordance with known methods depending on the sequence of interest (see, for example, Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York. Generally, by way of non-limiting example, stringent conditions may be about 5° C. lower than the thermal melting point for the specific sequence at a defined ionic strength and pH.

Nucleotide, polynucleotide, or nucleic acid molecule as used herein will be understood as including, where appropriate, both double-stranded and single-stranded molecules in the monomeric and dimeric (so-called in tandem) forms, and the transcription products thereof.

It will be understood that functional variants of winter aconite EhELO1 elongase enzyme may be possible, and are included within the scope of the invention. A variant of a winter aconite EhELO1 elongase enzyme may include any suitable enzyme having an amino acid sequence that varies from that of the unmodified sequence as shown in SEQ ID NO: 4, but that still encodes a protein that is functionally the same or similar to the unmodified gene product. By way of example, it will be understood that one or more conservative amino acid substitutions as described herein may be possible which do not substantially affect the function of the gene product. Other mutations, such as insertions, deletions, or substitutions, may also be possible, so long as enzyme function is not destroyed.

In embodiments where the transgenic organism is itself capable of producing sufficient fatty acid substrate for the elongase, no further supply of substrate fatty acid may be needed. By way of example, the transgenic organism may an oleaginous transgenic organism that produces 20:2-11,14 fatty acid, 20:3-11,14,17 fatty acid, 18:2-9,12 fatty acid, 18:3-9,12,15 fatty acid, or a combination thereof, either naturally or as a result of genetic engineering. In certain further embodiments, the transgenic organism may be a transgenic organism that expresses (either naturally or heterologously) a second elongase that further produces the substrate fatty acids 20:2-11,14 fatty acid, 20:3-11,14,17 fatty acid, or both. By way of example, the second elongase that produces 20:2-11,14 fatty acid, 20:3-11,14,17 fatty acid, or both, may be *Conidiobolus thromboides* elongase CtELO6 (the polypeptide encoded by SEQ ID NO: 7), or a variant or functional equivalent thereof.

In another embodiment, there is provided herein a nucleic acid molecule, expression vector, phage, or plasmid comprising a nucleotide sequence encoding the elongase, or a variant thereof.

In certain embodiments, there is provided herein a nucleic acid, expression vector, phage, or plasmid comprising a nucleic acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity to the nucleic acid of SEQ ID NO: 3, SEQ ID NO: 5, or SEQ ID NO: 6. In certain further embodiments, there is provided herein a nucleic acid, expression vector, phage, or plasmid comprising a nucleic acid sequence encoding an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity to the amino acid sequence of SEQ ID NO:4.

Such nucleic acids molecules, expression vectors, phages, or plasmids may, in certain embodiments, further comprise a nucleotide sequence encoding for an elongase that produces 20:2-11,14 fatty acid, 20:3-11,14,17 fatty acid, or both, such as (but not limited to) *Conidiobolus thromboides* elongase CtELO6 gene, or a variant thereof.

In certain other embodiments, nucleic acid molecules, expression vectors, phages, or plasmids as described herein may be for use in combination with a nucleic acid molecule, expression vector, phage, or plasmid comprising a nucleotide sequence encoding for an elongase which produces 20:2-11,14 fatty acid, 20:3-11,14,17 fatty acid, or both, such as (but not limited to) *Conidiobolus thromboides* elongase CtELO6 gene, or a variant thereof. An example of a suitable elongase may be the CTELO6 gene, the coding region cDNA sequence of which is shown in SEQ ID NO: 7.

Variants of the *Conidiobolus thromboides* elongase CtELO6 gene include, for example a nucleic acid molecule having at least 95% sequence identity to the nucleotide sequence set forth in SEQ ID NO:7 and a nucleic acid molecule having a codon degenerate nucleotide sequence of SEQ ID NO:7. Variants of the *Conidiobolus thromboides* elongase CtELO6 enzyme include, for example, an enzyme comprising an amino acid sequence having at least 95% sequence identity to the amino acid sequence encoded by SEQ ID NO: 7 and a conservatively substituted amino acid sequence of the amino acid sequence encoded by SEQ ID NO: 7.

It will be understood that compositions comprising or consisting of one or more of the nucleic acid molecules, polypeptides, expression vectors, phages, plasmids, and/or cells as described herein are also contemplated. Compositions may additionally comprise one or more physiologically acceptable diluents, carriers, excipients, or buffers, for example.

It will further be understood that in another embodiment, there is provided herein a nucleic acid molecule comprising a cDNA sequence encoding an EhELO1 elongase enzyme (SEQ ID NO: 4), or a cDNA sequence having a nucleotide sequence as set forth in SEQ ID NO: 5 or SEQ ID NO: 6. Such cDNA sequences differ from the naturally occurring sequence of the EhELO1 elongase gene due to the absence of introns, for example. Included within the scope of the invention is a nucleic acid molecule:

a) that is a complement of EhELO1 elongase gene, SEQ ID NO: 3, SEQ ID NO: 5, or SEQ ID NO: 6;

b) that is capable of hybridizing to EhELO1 elongase gene, SEQ ID NO: 3, SEQ ID NO: 5, or SEQ ID NO: 6 under stringent hybridization conditions; or c) that comprises a nucleic acid sequence with at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% sequence identity with the EhELO1 elongase gene, SEQ ID NO: 3, SEQ ID NO: 5, or SEQ ID NO: 6, or the nucleic acid molecule defined in a), b), or c).

The nucleic acid molecule may also be characterized by a range of sequence identities, for example ranging between any two of the percentages outlined above. Intermediate values, such as 76.6% and 93.17%, and ranges between intermediate values are also contemplated.

As discussed above, there is currently no commercial source for DDA or DTA. Accordingly, in a further embodiment there is provided herein a fatty acid product comprising isolated docosadienoic acid (DDA), isolated docosatrienoic acid (DTA), or an isolated DDA and DTA mixture, which has been produced by any of the method or methods described herein. Isolated DDA, isolated DTA, or an isolated DDA and DTA mixture may be obtained using a purification step as described herein, using a feedstock enrichment approach as described herein, using a transgenic organism that produces an enriched fatty acid substrate as described herein, or any combination thereof, for example. It will be understood that fatty acid products as described herein may be for use in any of a range of applications known to the person of skill in the art. By way of example, such fatty acid products may be for use in nutraceutical, pharmaceutical (i.e. antioxidant, anticancer, or anti-inflammatory), supplement, cosmetic, and/or personal care (i.e. lipstick, moisturizer, or makeup) product applications.

It will be understood that transgenic organisms may produce a long or very long chain unsaturated fatty acid, such as DDA, DTA, or both, as part of a novel whole oil. Accordingly, there is provided herein a whole oil comprising DDA, DTA, or both, produced by any of the method or methods described herein. The whole oil may be an edible food product. Such a whole oil may be used directly, or may be further purified to obtain enriched or pure DDA, DTA, or a mixture thereof, according to the particular application contemplated. In certain embodiments, a purification step may be employed wherein the DDA, DTA, or both, produced by the transgenic organism is purified to provide an isolated DDA sample, an isolated DTA sample, or an isolated DDA and DTA mixture sample. Such a purification step may involve the removal of undesirable components of the whole oil. For example, very short chain fatty acids may be removed by distillation. Also, where the transgenic organism produces a whole oil including erucic acid and the application is for humans, a purification step reducing or removing erucic acid from the whole oil may be desirable.

The following Examples are provided for illustrative purposes and are intended for the person of skill in the art. It will be understood that these examples are intended to be non-limiting, and that a number of variations and modifications, as will be known to the person of skill in the art having regard to the teachings herein, may be possible.

Example 1: Growing of *E. hyemalis* for Tissue Sampling

In order to obtain developing seeds for study, bulbs of *E. hyemalis* were planted in soil and kept in the dark at 4° C. for one month. After vernalization, bulbs started to germinate and grow. After flowering, the developing pods were labeled. Developing seeds at various stages (two to three weeks old after flowering) were harvested and used for subsequent study including fatty acid analysis and total RNA isolation.

Example 2: Fatty Acid Analysis of *E. hyemalis* Seeds

The fatty acid composition of *E. hyemalis* seeds at various stages of development was analyzed using gas chromatography (GC).

Bulk developing seeds were crushed with a glass rod, and FAMEs (fatty acid methyl esters) were derived using 3 N Methanolic HCl at 80° C. for 1 hr. Total FAMEs were extracted twice with water and hexane. Two microliter samples of total FAMEs were analyzed on an Agilent 6890N gas chromatograph equipped with a DB-23 column (30 m×0.25 mm) with 0.25-μm film thickness (J&W Scientific). The column temperature was maintained at 160° C. for 1 min, then increased to 240° C. at a rate of 4° C./min. Fatty acids were identified according to retention times of authentic fatty acid standards. The total fatty acid compositions as determined by GC analysis from developing seeds of *E. hyemalis* are shown in Table 3 below. As shown, the developing seeds produced DDA at the level of about 60% of the total fatty acids. Thus, these results indicated that obtained seeds could be used to isolate total RNA for cloning of gene(s) potentially encoding for elongase(s) involved in the synthesis of DDA.

TABLE 3

Total Fatty Acid Compositions of Developing Seeds Extracted from *E. hyemalis* 2-3 Weeks Post Flowering

| Fatty acid composition | Amount (% wt) |
|---|---|
| 16:0 + 16:1-Δ5 | 1.407 |
| 18:0 + 18:1-Δ5 | 1.405 |
| 18:1-Δ9 | 2.354 |
| 18:2-Δ9, Δ12 | 7.320 |
| 18:3-Δ9, Δ12, Δ15 | 0.660 |
| 20:0 | trace |
| 20:1-Δ5 | 3.858 |
| 20:1-Δ11 | 1.416 |
| 20:2-Δ11, Δ14 | 9.450 |
| 20:3, Δ5, Δ11, 14 | 8.535 |
| 22:1-Δ13 | 1.394 |
| 22:2-Δ13, Δ16 | 59.703 |
| 22:3-Δ5, Δ13, Δ16 | 1.680 |
| other | 0.818 |

Example 3: RNA Isolation and Sequencing

The high quantity of DDA fatty acid (22:2-13cis,16cis; up to 59.7%) found in developing seeds of *E. hyemalis* suggested that the developing seeds from *E. hyemalis* may be a good resource for identifying gene(s) involved in the biosynthesis of DDA. In order to identify candidate gene(s), total RNA from about 20 developing seeds (2-3 weeks after flowering) was first isolated by TRIzol reagent (Invitrogen) prior to purifying by the RNeasy Plant Mini column. Genomic DNA contamination was eliminated by on-column DNaseI digestion step with RNase-free DNase set (Qiagen). The quality of total RNA was determined using both Bioanalyzer and gel electroporesis. The RNA integrity number (RIN) of this sample by Bioanalyzer was 9.5, indicating a good quality of the RNA sample. The sample was then sent for RNA-seq Illumina sequencing analysis.

Example 4: Bioinformatic Analysis of ESTs to Identify Gene Involved in the Synthesis and Assembly of DDA, Sequencing and Cloning of the EhELO1 cDNA The RNA transcripts in developing seeds were sequenced using the Illumina RNA sequencing facility. The bioinformatics analysis of sequences showed there were two short contigs found in a gene which was homologous to ELO-like elongases. This gene was given the designation EhELO1.

The first contig contained 563 bps at the 5' end of the cDNA including the start codon, while the second contained 461 bps located at 3' end of the cDNA including the stop codon. There was a 376 bps overlapped region. This sequence information from the two contigs was then used to obtain the full length sequence of the EhELO1 cDNA. PCR amplification of the full length EhELO1 cDNA was performed using Q5 polymerase with two specific primers (DM719: 5'TCTAGAATGGAGTCCATTTCTGCTAG-3' (SEQ ID NO: 1) and DM720: 5'-TCTAGATTAAACCAGCTTCT-TATCCTTG-3' (SEQ ID NO: 2)) designed from the sequence information of the two contigs. The 828 bp expected size of the PCR product was eluted from agarose gel, then cloned into pYES2.1 yeast expression vector (EhELO1/pYES2.1) as described below and sequenced. The recombinant plasmids extracted from three independent clones were sequenced. The sequencing results showed the ORF of EhELO1 encodes a polypeptide of 275-amino acids (SEQ ID NO: 4) with a molecular weight of 31.3 kDa. The BLAST results showed the protein had 54% identity to GNS1/SUR4 membrane protein family *A. thaliana* (AT3 G06470).

The cDNA nucleotide sequence and the translated ORF of full length EhELO1 including 5' and 3' untranslated regions are shown in SEQ ID NOs: 3 and 4, respectively. SEQ ID NO: 5 provides the coding sequence of SEQ ID NO:3. A codon optimized version of the coding sequence of SEQ ID NO: 3 is provided in SEQ ID NO: 6. Codon optimization was conducted according to codon usage in *Brassica*.

Example 5: Functional Analysis of EhELO1 from *E. hyemalis* by Expression in *S. cerevisiae*

To determine the function of EhELO1, a construct was prepared for transformation into the yeast *S. cerevisiae* (INVSc1). By way of example, EhELO1/pYES2.1 construct was prepared as follows:

The coding region of the cDNA was amplified by PCR using Q5 DNA polymerase (New England Biolabs) with primers DM719 (SEQ ID NO: 1) and DM720 (SEQ ID NO: 2) and cloned directly into pYES2.1 Topo-TA expression vector (Invitrogen) after Taq DNA polymerase treatment. The sequence of the insert was confirmed to be identical to the original cDNA and in the sense orientation relative to the GAL1 promoter.

To determine the function of EhELO1/pYES2.1, the construct was transformed into yeast *S. cerevisiae* (INVSc1). Expression was controlled by the GAL1 promoter. The yeast transformants were selected on -URA selective media and screened by colony PCR with specific primers. To assess the elongase activity, the PCR positive transformants were grown to saturation in 10 mL of synthetic yeast media containing 2% glucose, 0.67% bacto-yeast nitrogen base lacking uracil for 2 days at 28° C. The cultures were then washed twice with distilled water and induced with 10 mL of induction medium (synthetic yeast media containing 2% galactose) supplemented with or without 250 μM of eicosadienoic acid (20:2-11,14) substrates for the elongation activity to synthesize DDA in the presence of 0.1% tergitol. The induced cultures were incubated at 20° C. for 2 days to allow for adequate expression and the synthesis of new products.

Example 6: Fatty Acid Analysis of Transformed Yeast Cells

For fatty acid analysis of yeast cells, the cells were pelleted by centrifugation, washed once with 0.1% tergitol and once with water. The fatty acids were converted to their methyl esters with 3 N methanolic HCl at 80° C. for 1 hour. After addition of 1 mL of water, the sample was extracted twice with 2 mL of hexane. The hexane extract was combined and dried under $N_2$, and resuspended in 200 μL of hexane. The fatty acid composition was analyzed on a Hewlett-Packard 5890A gas chromatograph equipped with a DB-23 column (30-m×0.25-mm×0.25-μm). The temperature program was isothermal 160° C. for 1 min, gradient 4° C./min to 240° C., and then isothermal at 240° C. for 10 min. For GC/MS analysis of docosadienoic acid methyl ester, the sample was dried under a stream of nitrogen and the residue was dissolved in 100 μL of hexane. The analysis was accomplished using an Agilent 5973 mass selective detector coupled to an Agilent 6890N gas chromatograph using G1701DA MSD Chemstation software (for instrument control and data analysis) and equipped with a 30-m×0.25-mm DB-23 column with 0.25-μm film thickness (J&W Scientific). The chromatograph conditions included a split injection (20:1) onto the column using a hydrogen flow of 0.4 ml/min, an initial temperature of 160° C. for 1 min, and a subsequent temperature ramp of 4° C./min to 240° C. The mass selective detector was run under standard electron impact conditions (70 eV), scanning an effective m/z range of 40-700 at 2.26 scans/s.

Figure 2:
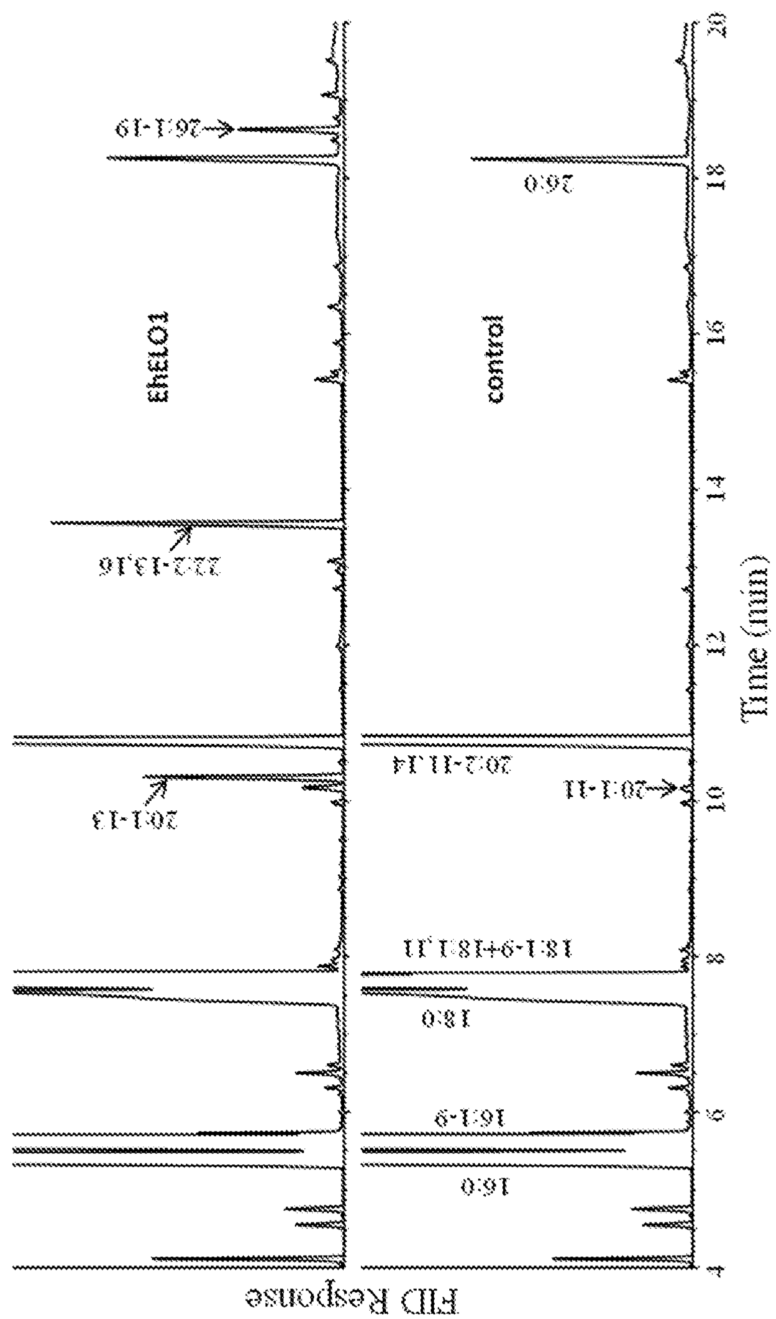
FIG. 2 shows a gas chromatograph analysis of fatty acid methyl esters obtained from yeast transformants containing either EhELO1/pYES2.1 (EhELO1) or pYES2.1 (control), supplemented with eicosadienoic acid (20:2-11,14)
Figure 3:
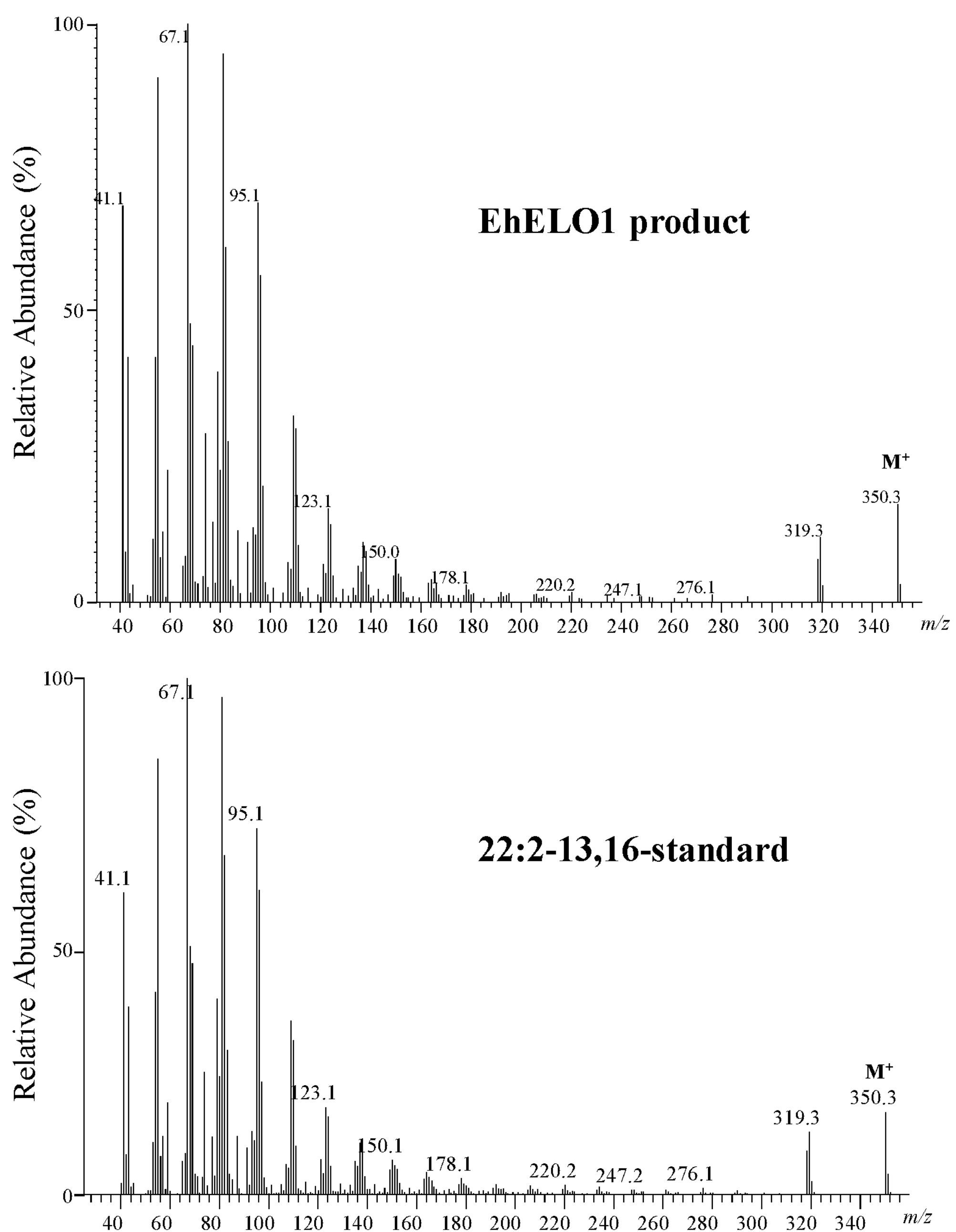
FIG. 3 shows a mass spectrum of the fatty acid methyl esters from the second new peak found in yeast transformants expressing EhELO1/pYES2.1 (EhELO1, top panel) as compared to the known standard, DDA (22:2:13,16-standard, bottom panel)

The total fatty acid product analysis indicated that in comparison with the vector control, the transformants expressing EhELO1 produced three new products (see FIG. 2). The second product had the retention time identical to that of DDA standard. GC/MS analysis of this peak confirmed that it was identical to the DDA standard (see FIG. 3) confirming that it is indeed DDA, 22:2-13,16. This result confirms that EhELO1 isolated from *E. hyemalis* encodes a functional elongase which catalyses the addition of a two carbon unit to the carboxyl end of the eicosadienoic fatty acid. The other products produced by the transformants were omega-7 fatty acids including 20:1-13 and 26:1-19 fatty acids, which were elongated from 18:1-11 to produce 20:1-13, 22:1-15, 24:1-17, and finally 26:1-19.

Example 7: Versatility of EhELO1 for the Conversion of a Variety of Fatty Acids in Yeast To define the diverse activity of the discovered elongase (EhELO1) from winter aconite, a variety of possible common fatty acids and unusual fatty acids that differ in the number and position of double bonds as well as in the chain length was exogenously supplied to the yeast transformant expressing the elongase EhELO1 for in vivo activity assays. The conversion of substrates to products was measured and used for the comparison of elongation efficiencies among fatty acid substrates.

The EhELO1 coding sequence was released from plasmid, EhELO1/pYES2.1 and sub-cloned into another yeast expression vector pHVX2 under the control of phosphoglycerate kinase 1 constitutive promoter, giving a plasmid EhELO1/pHVX2. The recombinant plasmid was transformed into *Saccharomyces cerevisiae* INVSc1. The yeast transformants with either EhELO1 or empty vector pHVX2 were grown at 30° C. for 1 day. The overnight cultures were diluted to an $OD_{600}$ of 0.1 in the same medium supplemented with or without 0.25 mM of various free fatty acids in the presence of tergitol. After incubation at 20° C. for 2 days, yeast cells were harvested and washed once with tergitol and once with water. Total fatty acids in yeast transformants were converted to FAMES by an acid transmethylation process and analyzed by gas chromatography.

As shown in Table 4, polyunsaturated fatty acids from 18 C to 22 C with two to five double bonds were favorable substrates for EhELO1 with 20:3-11,14,17 being the most preferred. However, this elongase was also highly active on some mono-unsaturated fatty acids such as 18:1-11.

TABLE 4

Elongation Efficiency on Fatty Acid Substrates by EhELO1 in *Saccharomyces cerevisiae Saccharomyces cerevisiae*. Numbers were calculated from the peak area of FAMEs. Values are means of four replicates with standard deviation.

| Substrate | Product | Elongation efficiency (%) |
|---|---|---|
| 18:1-9 | 20:1-11 | 3.3 ± 0.07 |
| 20:1-11 | 22:1-13 | 12.6 ± 0.23 |
| 22:1-13 | No reaction | 0.0 ± 0.0 |
| 18:1-11 | 20:1-13 | 49.4 ± 1.79 |
| 18:1-OH | No reaction | 0.0 ± 0.0 |
| 18:2-9, 12 (linoleic acid) | 20:2-11, 14 | 44.6 ± 3.26 |
| 20:2-11, 14 | 22:2-13, 16 (DDA, n-6) | 48.5 ± 2.12 |
| 22:2-13, 16 (DDA, n-6) | 24:2-15, 18 | 3.4 ± 0.17 |
| 18:3-9, 12, 15 ((linolenic acid) | 20:3-11, 14, 17 | 54.7 ± 0.83 |
| 20:3-11, 14, 17 | 22:3-13, 16, 19 (DTA, n-3) | 61.8 ± 0.35 |
| 22:3-13, 16, 19 (DTA, n-3) | 24:3-15, 18, 21 | 9.7 ± 0.13 |
| 18:3-6, 9, 12 (γ-linolenic acid) | 20:3-8, 11, 14 | 28.3 ± 1.95 |
| 20:3-8, 11, 14 | 22:3-10, 13, 16 | 46.4 ± 1.44 |
| 18:4-6, 9, 12, 15 (SDA) | 20:4-8, 11, 14, 17 | 25.0 ± 0.37 |
| 20:4-8, 11, 14, 17 | 22:4-10, 13, 16, 19 | 50.3 ± 0.53 |
| 22:4-10, 13, 16, 19 | 24:4-12, 15, 18, 21 | 32.7 ± 0.49 |
| 20:4-5, 8, 11, 14 (ARA) | 22:4-7, 10, 13, 16 | 36.2 ± 0.92 |
| 22:4-7, 10, 13, 16 | 24:4-9, 12, 15, 18 | 20.5 ± 0.37 |
| 20:5-5, 8, 11, 14, 17 (EPA) | 22:5-7, 10, 13, 16, 19 (DPA) | 39.8 ± 0.43 |
| 22:5-7, 10, 13, 16, 19 (DPA) | 24:5-9, 12, 15, 18, 21 | 31.9 ± 0.19 |
| 22:6-4, 7, 10, 13, 16, 19 (DHA) | 24:6-6, 9, 12, 15, 18, 21 | 10.8 ± 0.52 |

Example 8: Expression of EhELO1 from *E. hyemalis* in *Camelina*

Figure 4:
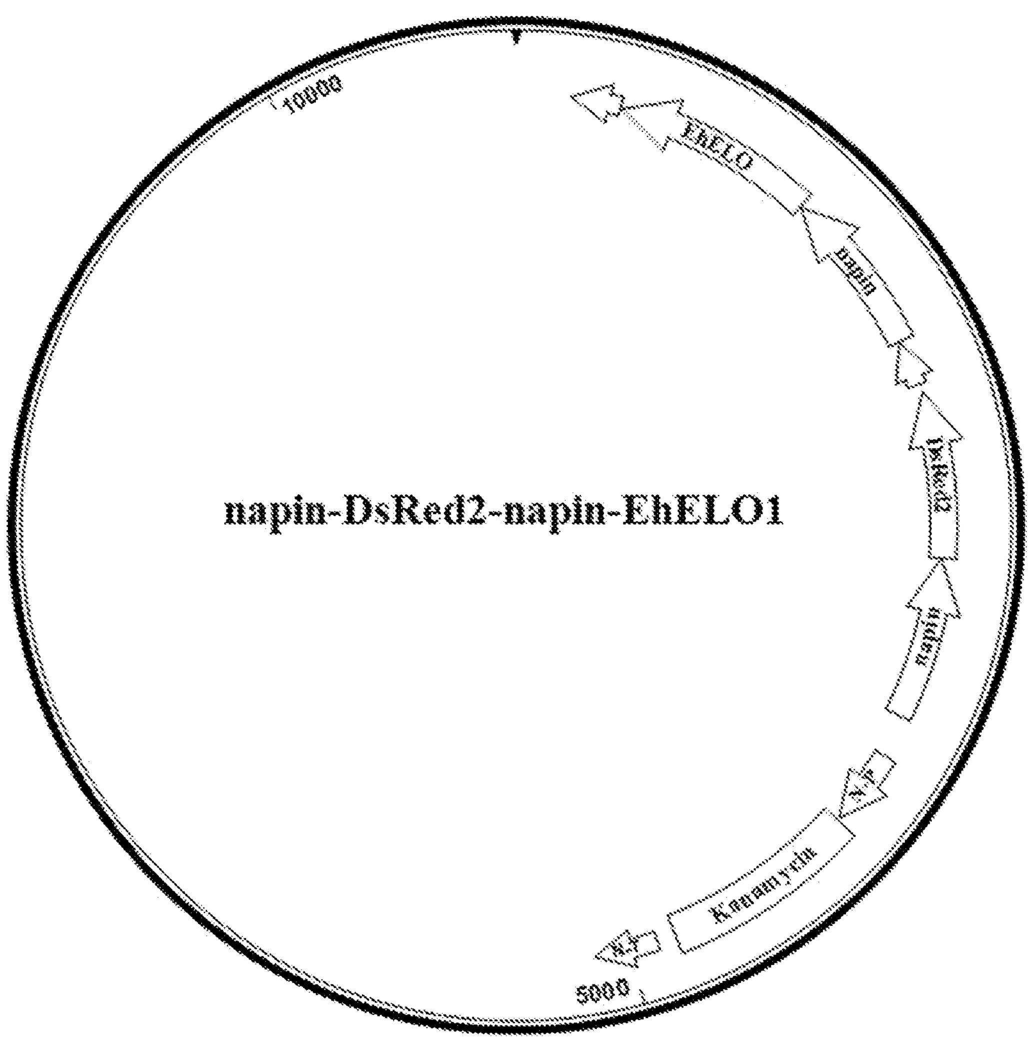
FIG. 4 shows a plant expression vector containing EhELO1 and DsRed2 under napin promoter (DE plasmid) used for generating transgenic *Camelina sativa* and *Arabidopsis;*
Figure 5:
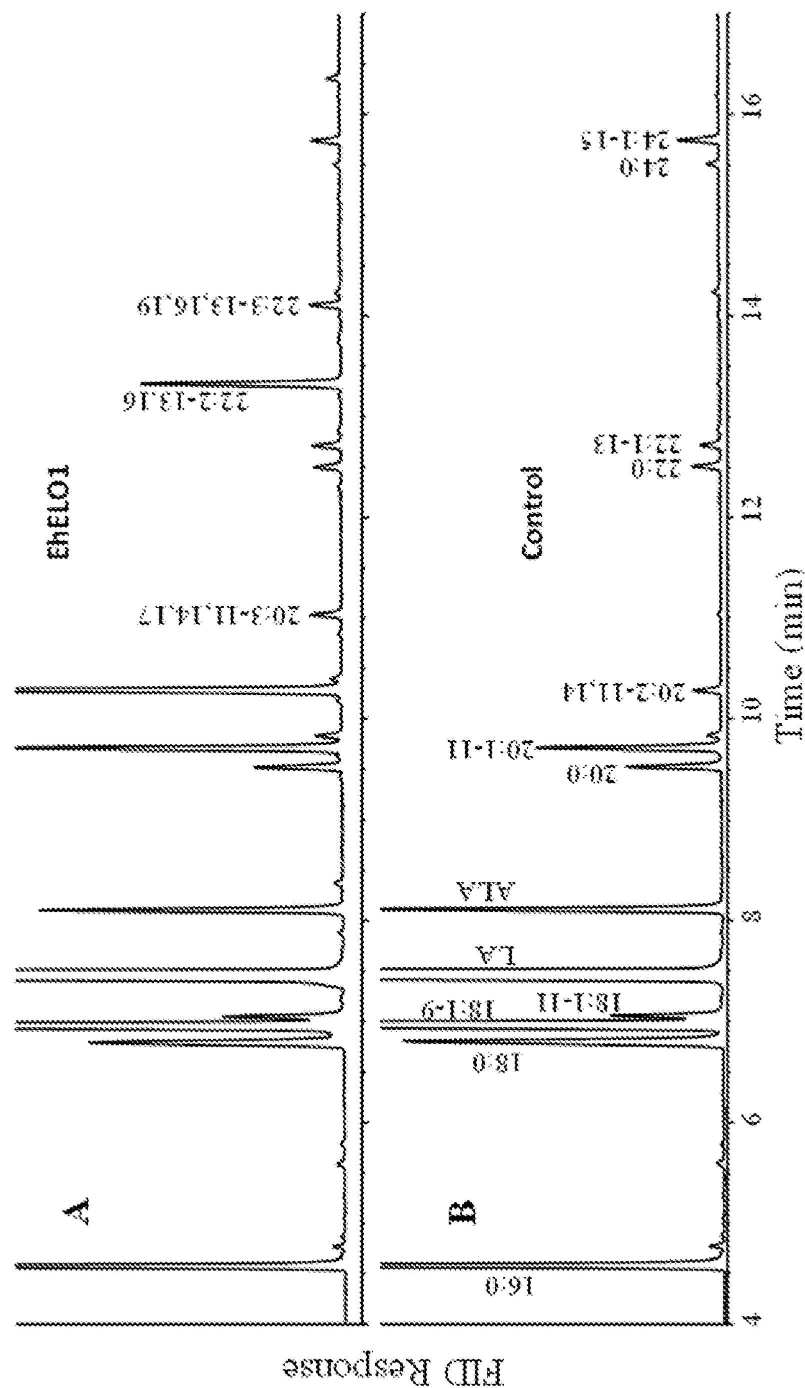
FIG. 5 shows production of DDA in *Camelina sativa* by seed-specific expression of EhELO1. (A) GC analysis of fatty acid methyl esters prepared from transgenic *Camelina* expressing EhELO1. (B) GC analysis of fatty acid methyl esters prepared from the *Camelina* control.

To confirm that EhELO1 is functional in heterologous oilseed plants, the gene was expressed under the control of seed-specific *Brassica napus* napin storage protein promoter along with a red florescent protein gene (FIG. 4) as selection marker and kanamycin resistant gene in *Camelina sativa*. The correct construct was introduced into *Agrobacterium tumefaciens* strain GV3101 (pMP90) by electroporation. The recombinant plasmid containing the candidate gene was introduced by the in-planta *Agrobacterium*-infiltration approach into a *C. sativa* fad3 and fae1 RNAi line that is low in 20:1-11 and 18:3-9,12,15, providing a higher level of the substrate (linoleic acid) for EhELO1 to synthesize docosadienoic acid. *Camelina* plants were dipped in the *Agrobacterium* transformant carrying the construct for 30 sec with gentle agitation. The dipped plants were laid horizontally in trays and covered with plastic lids to maintain high humidity. The dipped plants ($T_0$) were placed in the dark for 24 hrs and moved to the growth chamber at 22° C. under a 16-hr-light (120 $\mu Em^{-2}s^{-1}$) until mature. This method has been demonstrated by many laboratories as being effective to transform both the plants. When the plants were mature, dry seeds were harvested and labeled as $T_1$ seeds. Putative transgenic seeds were selected based on either kanamycin resistance or DsRed2 expression. Using this approach, 16 transgenic *Camelina* plants were produced. Fatty acid analysis of the single seed showed the *E. hyemalis* elongase was active in *Camelina*. As shown in FIG. 5, compared to the untransformed mutant control line, transgenic *Camelina* produced three new fatty acids, 20:3-11,14,17, 22:3-13,16, 19 and 22:2-13,16. Among them, 22:2-13,16 is the most abundant (see Table 5) fatty acid among the new fatty acids produced. Table 5 shows the detailed fatty acid compositions of 16 transgenic *Camelina* by weight percentage compared with 3 untransformed seeds. Thirty one *Camelina* transgenic seeds were selected by fluorescence of DsRed2 and grown for the next generation ($T_2$ seeds).

TABLE 5

Fatty Acid Compositions in Transgenic Camelina sativa fad 3 and fae 1 RNAi line (Values are represented as the weight percentage of total fatty acids (% TFA))

| | | Fatty Acid | | | | | | | | | | | | | |
|---|---|---|---|---|---|---|---|---|---|---|---|---|---|---|---|
| | | 16:0 | 18:0 | 18:1-9c | 18:1-11c | 18:2 | 18:3 | 20:0 | 20:1 | 20:2 | 22:0 | 22:1 | 22:2 | 24:0 | 24:1 |
| Line | Control-1 | 8.44 | 4.16 | 18.88 | 1.38 | 57.83 | 4.37 | 1.11 | 2.29 | 0.38 | 0.33 | 0.35 | 0.00 | nd | 0.49 |
| | Control-2 | 14.1 | 7.19 | 21.09 | 1.69 | 47.35 | 2.22 | 1.55 | 1.89 | 1.10 | 0.57 | 0.00 | 0.00 | nd | 1.24 |
| | Control-3 | 8.15 | 3.55 | 17.44 | 1.54 | 60.77 | 4.55 | 0.88 | 1.83 | 0.39 | 0.25 | 0.26 | 0.00 | nd | 0.39 |
| | T1-1 | 7.62 | 3.92 | 18.62 | 1.18 | 50.48 | 4.23 | 1.09 | 3.86 | 5.63 | 0.35 | 0.45 | 2.07 | nd | 0.51 |
| | T1-2 | 9.54 | 5.57 | 15.49 | 1.44 | 52.40 | 7.50 | 1.75 | 3.27 | 0.80 | 0.57 | 0.67 | 0.25 | nd | 0.75 |
| | T1-3 | 8.40 | 4.96 | 15.92 | 1.24 | 50.57 | 5.76 | 1.35 | 3.51 | 5.64 | 0.41 | 0.51 | 1.10 | nd | 0.63 |
| | T1-4 | 7.37 | 4.26 | 20.60 | 1.16 | 52.91 | 3.99 | 1.11 | 2.78 | 3.75 | 0.36 | 0.38 | 0.86 | nd | 0.48 |
| | T1-5 | 7.41 | 4.20 | 16.93 | 1.15 | 51.09 | 4.36 | 1.14 | 3.76 | 6.35 | 0.33 | 0.51 | 2.31 | 0.10 | 0.49 |
| | T1-6 | 6.96 | 4.20 | 19.96 | 1.25 | 52.22 | 4.12 | 1.01 | 3.04 | 5.10 | 0.3 | 0.36 | 0.99 | nd | 0.47 |
| | T1-7 | 7.31 | 4.35 | 21.37 | 1.18 | 51.90 | 4.30 | 1.08 | 2.76 | 4.06 | 0.29 | 0.32 | 0.62 | nd | 0.45 |

TABLE 5-continued

Fatty Acid Compositions in Transgenic Camelina sativa fad 3 and fae 1 RNAi line (Values are represented as the weight percentage of total fatty acids (% TFA))

| | Fatty Acid | | | | | | | | | | | | | |
|---|---|---|---|---|---|---|---|---|---|---|---|---|---|---|
| | 16:0 | 18:0 | 18:1-9c | 18:1-11c | 18:2 | 18:3 | 20:0 | 20:1 | 20:2 | 22:0 | 22:1 | 22:2 | 24:0 | 24:1 |
| T1-8 | 7.69 | 3.85 | 16.39 | 1.26 | 50.28 | 5.87 | 1.06 | 3.52 | 6.07 | 0.32 | 0.5 | 2.66 | nd | 0.53 |
| T1-9 | 7.71 | 3.62 | 19.57 | 1.23 | 51.16 | 5.20 | 1.09 | 3.93 | 4.27 | 0.34 | 0.55 | 0.70 | 0.15 | 0.62 |
| T1-10 | 7.26 | 3.89 | 18.74 | 1.21 | 52.58 | 3.74 | 1.00 | 2.96 | 5.73 | 0.31 | 0.38 | 1.75 | nd | 0.45 |
| T1-11 | 8.03 | 4.18 | 17.92 | 1.27 | 49.98 | 4.69 | 1.23 | 4.12 | 5.65 | 0.33 | 0.61 | 1.43 | 0.14 | 0.56 |
| T1-12 | 8.12 | 3.98 | 17.45 | 1.52 | 50.08 | 5.85 | 1.03 | 3.52 | 5.90 | 0.31 | 0.49 | 1.25 | nd | 0.51 |
| T1-13 | 7.76 | 4.23 | 20.23 | 1.32 | 51.82 | 4.42 | 1.08 | 2.88 | 3.99 | 0.32 | 0.43 | 0.95 | nd | 0.57 |
| T1-14 | 7.28 | 4.28 | 23.17 | 1.20 | 50.84 | 3.90 | 1.07 | 2.68 | 3.78 | 0.35 | 0.35 | 0.60 | 0.12 | 0.50 |
| T1-15 | 7.03 | 4.73 | 23.19 | 1.36 | 53.63 | 3.11 | 1.06 | 1.98 | 2.27 | 0.35 | 0.25 | 0.55 | 0.1 | 0.49 |
| T1-16 | 6.97 | 3.7 | 23.06 | 1.45 | 50.44 | 3.55 | 0.91 | 2.99 | 4.69 | 0.29 | 0.35 | 1.18 | nd | 0.43 |

Example 9: Expression of EhELO1 from *E. hyemalis* in *Arabidopsis*

Figure 6:
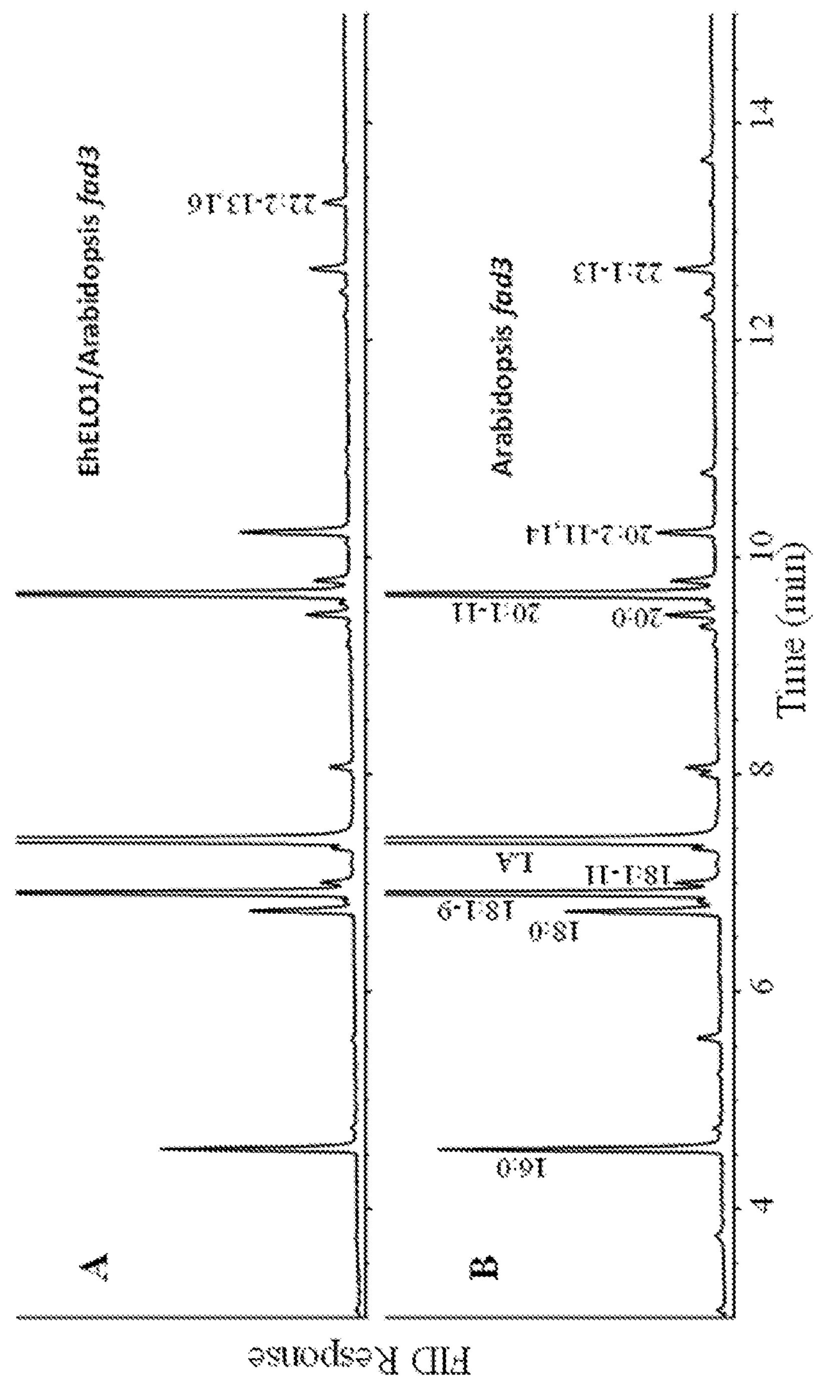
FIG. 6 shows production of DDA in *Arabidopsis thaliana* fad3 mutant by seed-specific expression of EhELO1. (A) GC analysis of fatty acid methyl esters prepared from three independent transgenic *Arabidopsis* expressing EhELO1. (B) GC analysis of fatty acid methyl esters prepared from the *Arabidopsis* control.

EhELO1 under the control of the seed-specific napin promoter was transformed into *Arabidopsis* (wildtype, fad3 mutant and fad3/fae1 double mutant) plants using the EhELO1 and DsRed2 plasmid construct (FIG. 5) and the floral-dip method as described above for *Camelina*. The transgenic seeds from the fad3 mutant were selected by fluorescence of DsRed2 and grown for the next generation ($T_2$ seeds). Fatty acid analysis of three independent fluorescent seeds showed the winter aconite elongase was active in *Arabidopsis* fad3 mutant plant. As seen in FIG. 6, compared to the untransformed mutant control, transgenic *Arabidopsis* mutant plant produced one new fatty acid identified as 22:2-13,16 (DDA). The amount of DDA was lower when compared to those in transgenic *Camelina* described above.

Example 10: Expression of EhELO1 from *E. hyemalis* in *Brassica carinata*

Figure 7:
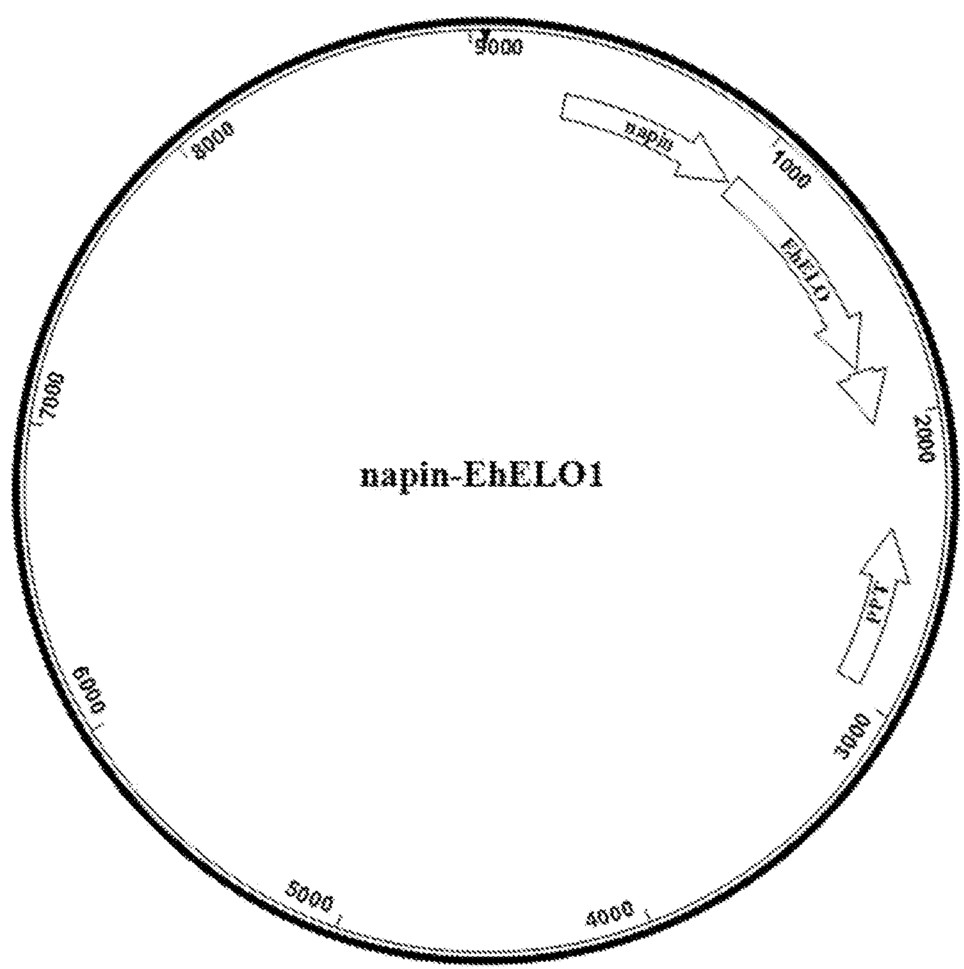
FIG. 7 shows a plant expression vector containing EhELO1 and PPT (phosphinothricin) selection marker under napin promoter used for generating transgenic *Brassica carinata;*
Figure 8:
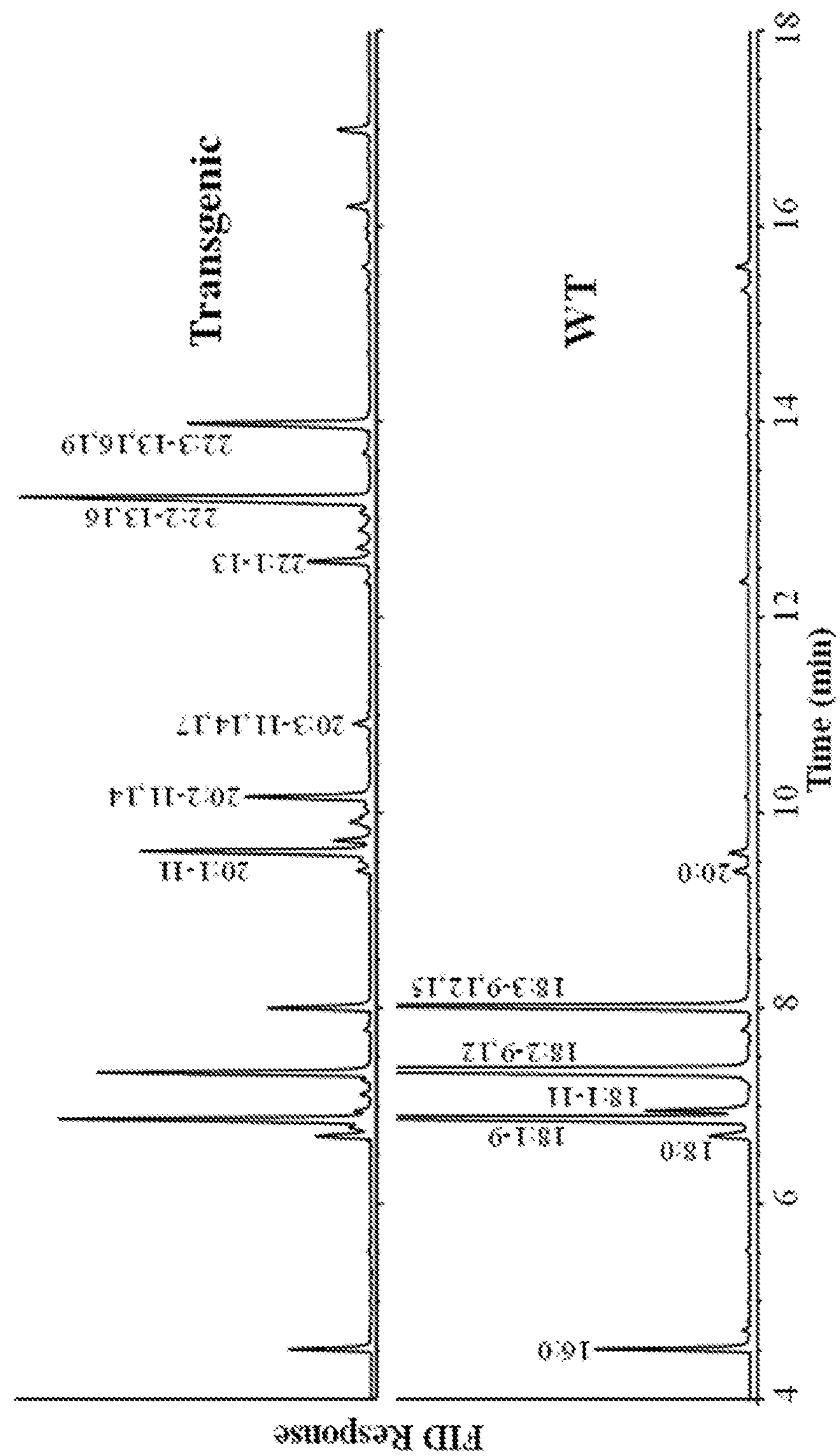
FIG. 8 shows gas chromatograms of the total fatty acids from EhELO1 transgenic *Brassica carinata* seeds as compared with untransformed wild type.

To produce DDA in *Brassica carinata*, a construct was made containing the EhELO1 gene under control of a seed-specific napin promoter along with PPT (phosphinothricin) selection marker was made (FIG. 7). The recombinant plasmid was introduced by an in-planta *Agrobacterium*-infiltration transformation into *Brassica carinata* with a high level of the substrate (linoleic acid). Using this approach, one transgenic plant was produced. Fatty acid analysis of a pool of 10 seeds from the transgenic plants showed the *E. hyemalis* elongase was highly active in the transgenic. FIG. 8 shows a GC analysis of the total fatty acids, the upper panel from transgenic *Brassica carinata* seeds and the lower panel from non-transformed wild type *Brassica carinata* seeds. As seen in FIG. 8, compared to the untransformed wild type, transgenic *Brassica carinata* produced two major new fatty acids, 22:2-13,16 and 22:3-13,16,19. Among them, DDA (22:2-13,16) is the most abundant (Table 6) reaching more than 20% of the total fatty acids.

TABLE 6

Fatty acid composition of transgenic Brassica carinata seeds (% of total fatty acids)

| | | Fatty Acid | | | | | | | | | | | | |
|---|---|---|---|---|---|---|---|---|---|---|---|---|---|---|
| | | 16:0 | 18:0 | 18:1-9 | 18:1-11 | 18:2-9, 12 | 18:3-9, 12, 15 | 20:0 | 20:1-11 | 20:2-11, 14 | 20:3-11, 14, 17 | 22:1-13 | 22:2-13, 16 | 22:3-13, 16, 19 |
| Line | Wild type | 5.26 | 2.07 | 24.25 | 3.91 | 41.65 | 19.63 | 0.66 | 0.84 | 0.16 | | | | |
| | Transgenic | 3.21 | 2.68 | 14.59 | 0.72 | 12.18 | 4.79 | 0.63 | 12.10 | 6.28 | 0.88 | 4.25 | 21.88 | 9.92 |

Example 11: Stability of Target Fatty Acids in Different Generations of Transgenic Seeds of *Brassica carinata*

To observe heritability of fatty acid compositions of transgenic seeds, one elite T1 line was grown to give T2 seeds, from which two elite T2 lines were selected and grown to give T3 seeds. As shown in Table 7, fatty acid compositions in the seeds were relatively stable among three generations and in fact two target fatty acids DDA and DTA were even slightly higher in T2 and T3 seeds than in T1 seeds.

TABLE 7

Fatty acid composition of transgenic Brassica carinata T1, T2, and T3 seeds.

| | | Fatty Acid | | | | | | | | | | | | |
|---|---|---|---|---|---|---|---|---|---|---|---|---|---|---|
| | | 16:0 | 18:0 | 18:1-9 | 18:1-11 | 18:2-9, 12 | 18:3-9, 12, 15 | 20:0 | 20:1-11 | 20:2-11, 14 | 20:3-11, 14, 17 | 22:1-13 | 22:2-13, 16 | 22:3-13, 16, 19 |
| Line | Wild type | 5.26 | 2.07 | 24.25 | 3.91 | 41.65 | 19.63 | 0.66 | 0.84 | 0.16 | — | — | — | — |
| | T1-1 | 3.21 | 2.68 | 14.59 | 0.72 | 12.18 | 4.79 | 0.63 | 12.10 | 6.28 | 0.88 | 4.25 | 21.88 | 9.92 |
| | T2-13 | 3.19 | 2.25 | 12.71 | 0.74 | 16.23 | 4.03 | 0.49 | 7.78 | 7.35 | 0.64 | 2.32 | 28.55 | 7.87 |
| | T2-30 | 2.85 | 2.35 | 11.16 | 0.66 | 14.56 | 5.76 | 0.64 | 8.33 | 5.10 | 0.60 | 3.82 | 26.13 | 10.41 |
| | T3-13 | 3.54 | 2.10 | 12.54 | 0.98 | 17.22 | 5.03 | 0.49 | 8.48 | 7.34 | 0.70 | 2.32 | 27.66 | 8.60 |
| | T3-30 | 3.54 | 2.67 | 14.57 | 0.88 | 15.40 | 5.51 | 0.69 | 11.66 | 6.78 | 0.79 | 2.96 | 23.03 | 8.96 |

Example 12: Expression of EhELO1 from *E. hyemalis* in Combination with Expression of CtELO6 Elongase from *Conidiobolus thromboides*

Figure 9:
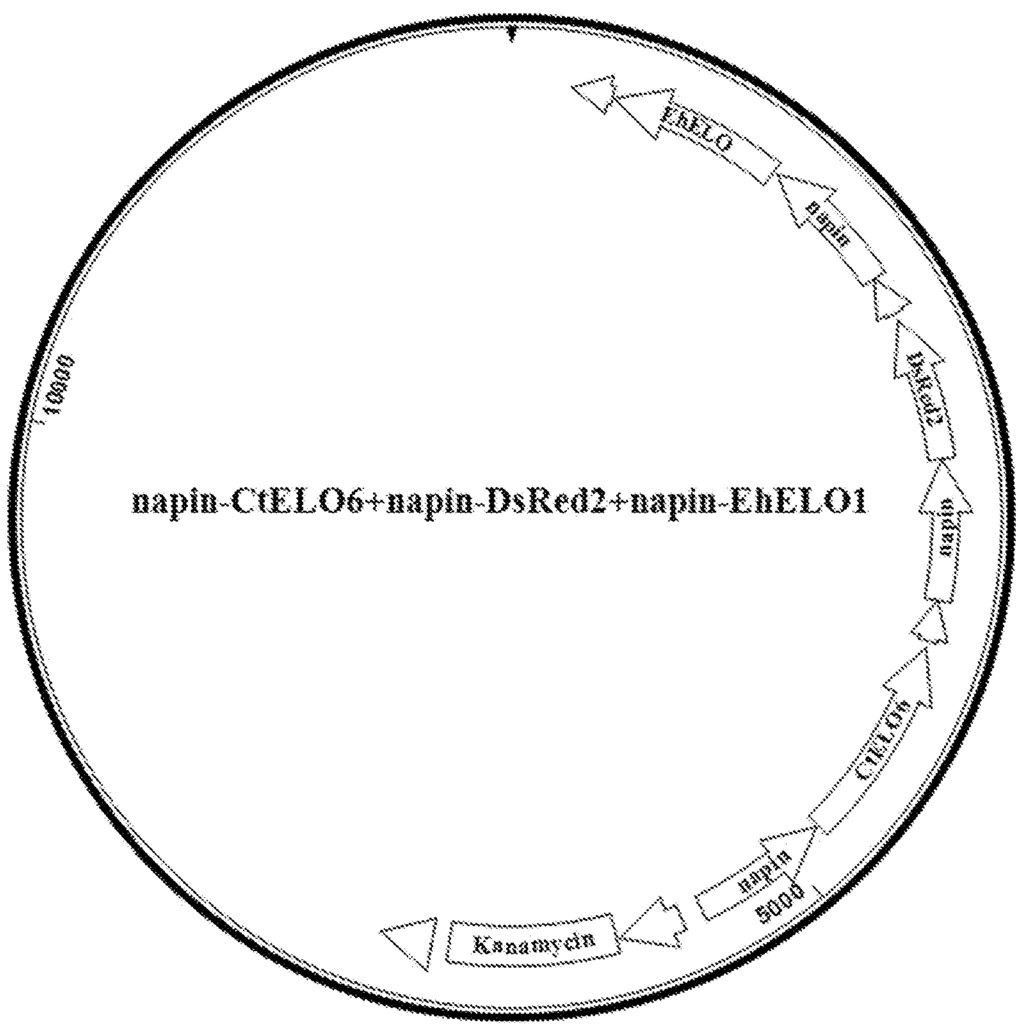
FIG. 9 shows a plant expression vector containing EhELO1, DsRed2, and CtELO6 under napin promoter (DEE6 plasmid).

A new plant expression plasmid with a three gene cassette containing EhELO1 from winter aconite, an elongase from *Conidiobolus thromboides* (CtELO6) (SEQ ID NO: 7), and DsRed2 was constructed in an effort to enhance production of 20:2-11,14 fatty acid as a substrate for EhELO1 to produce DDA (expression cassette shown in FIG. 9). The plasmid was confirmed by sequencing and will be transformed into either *Camelina* or *Arabidopsis.*

The function of elongase CtELO6 has been studied in yeast, *Saccharomyces cerevisiae*, wherein it has been observed to elongate 18:2:9,12 fatty acid with an elongation efficiency of more than 20%. Accordingly, it is expected that the production of 20:2:11,14 by CtELO6 in plants may provide increased substrate for EhELO1, providing enhanced production of DDA in plants expressing both CtELO6 and EhELO1.

Illustrative embodiments have been described by way of the above examples. It will be understood to persons skilled in the art that a number of variations and modifications may be made without departing from the scope of the invention as defined in the claims.

What is claimed is:

1. An isolated nucleic acid molecule comprising a nucleotide sequence encoding a polypeptide having elongase activity, wherein said polypeptide has at least 95% sequence identity to the full length of the amino acid sequence set forth in SEQ ID NO: 4, and wherein the nucleotide sequence comprises at least one nucleotide substitution, insertion, or non-terminal deletion relative to the nucleotide sequence set forth in SEQ ID NO: 5.

2. The isolated nucleic acid molecule of claim 1, wherein the nucleic acid molecule comprises the nucleotide sequence set forth in SEQ ID NO: 6.

3. An expression vector, phage, or plasmid comprising a nucleic acid molecule, said nucleic acid molecule comprising:

i) the nucleotide sequence set forth in SEQ ID NO: 5;

ii) the nucleotide sequence set forth in SEQ ID NO: 6; or iii) a nucleotide sequence encoding a polypeptide having elongase activity, wherein said polypeptide has at least 95% sequence identity to the full length of the amino acid sequence set forth in SEQ ID NO: 4, wherein said nucleic acid molecule is operably linked to a heterologous regulatory element.

4. A transgenic organism, genetically modified seed, or genetically modified cell comprising the nucleic acid molecule defined in claim 3.

5. The transgenic organism, genetically modified seed, or genetically modified cell of claim 4, wherein the transgenic organism is a plant or microbe.

6. The transgenic organism, genetically modified seed, or genetically modified cell of claim 5, wherein the transgenic organism, genetically modified seed, or genetically modified cell is a *Camelina sativa* or *Brassica carinata* plant, seed, or cell.

7. A method for producing at least one unsaturated fatty acid comprising 20 or more carbons, said method comprising:

i) providing a transgenic organism comprising the nucleic acid molecule defined in claim 3;

ii) expressing the nucleic acid molecule in the transgenic organism; and iii) allowing the transgenic organism to produce the at least one unsaturated fatty acid.

8. The method of claim 7, wherein the at least one unsaturated fatty acid is a C20, C22, or C24 unsaturated fatty acid.

9. The method of claim 7, wherein the at least one unsaturated fatty acid is 20:1-11 fatty acid; 20:1-13 fatty acid; 22:1-13 fatty acid; 22:1-15 fatty acid; 24:1-17 fatty acid; 26:1-19 fatty acid; 20:2-11,14 fatty acid; 22:2-13,16 fatty acid; 24:2-15,18 fatty acid; 20:3-11,14,17 fatty acid; 22:3-13,16,19 fatty acid; 24:3-15,18,21 fatty acid; 20:3-8,11,14 fatty acid; 22:3-10,13,16 fatty acid; 20:4-8,11,14,17 fatty acid; 22:4-10,13,16,19 fatty acid; 24:4-12,15,18,21 fatty acid; 22:4-7,10,13,16 fatty acid; 24:4-9,12,15,18 fatty acid; 22:5-7,10,13,16,19 fatty acid; 24:5-9,12,15,18,21 fatty acid; 24:6-6,9,12,15,18,21 fatty acid; or a combination of two or more thereof.

10. The method of claim 7, wherein the at least one unsaturated fatty acid is docosadienoic acid (DDA), docosatrienoic acid (DTA), or a combination of both DDA and DTA.

11. The method of claim 7, wherein the transgenic organism is provided with a feedstock comprising 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof.

12. The method of claim 11, wherein the feedstock comprises 20:2-11,14 fatty acid or 20:3-11,14,17 fatty acid.

13. The method of claim 7, wherein the transgenic organism is an oilseed plant or a microbe.

14. The method of claim 13, wherein the oilseed plant is *Camelina sativa* or *Brassica carinata*.

15. The method of claim 7, wherein the transgenic organism is an oleaginous transgenic organism that produces 20:2-11,14 fatty acid, 20:3-11,14,17 fatty acid, 18:2-9,12 fatty acid, 18:3-9,12,15 fatty acid, or a combination of one or more thereof.

16. The method of claim 7, wherein the transgenic organism expresses a second elongase enzyme that produces 20:2-11,14 fatty acid, 20:3-11,14,17 fatty acid, or both.

17. An ex vivo method for producing at least one unsaturated fatty acid comprising 20 or more carbons from a substrate feedstock, the method comprising:

a) providing the substrate feedstock; and b) exposing the substrate feedstock to a polypeptide having elongase activity, wherein said polypeptide has at least 95% sequence identity to the full length of the amino acid sequence set forth in SEQ ID NO: 4, wherein the substrate feedstock comprises 18:1-9 fatty acid; 18:1-11 fatty acid; 20:1-11 fatty acid; 20:1-13 fatty acid; 22:1-15 fatty acid; 24:1-17 fatty acid; 18:2-9,12 fatty acid; 20:2-11,14 fatty acid; 22:2-13,16 fatty acid; 18:3-9,12,15 fatty acid; 20:3-11,14,17 fatty acid; 22:3-13,16,19 fatty acid; 18:3-6,9,12 fatty acid; 20:3-8,11,14 fatty acid; 18:4-6,9,12,15 fatty acid; 20:4-8,11,14,17 fatty acid; 22:4-10,13,16,19 fatty acid; 20:4-5,8,11,14 fatty acid; 22:4-7,10,13,16 fatty acid; 20:5-5,8,11,14,17 fatty acid; 22:5-7,10,13,16,19 fatty acid; 22:6-4,7,10,13,16,19 fatty acid; or a combination of two or more thereof.

18. The method of claim 17, wherein the feedstock comprises 20:2-11,14 fatty acid or 20:3-11,14,17 fatty acid.

19. The method of claim 17, wherein a second elongase enzyme that produces 20:2-11,14 fatty acid, 20:3-11,14,17 fatty acid, or both, is used to enrich the substrate feedstock with 20:2-11,14 fatty acid, 20:3-11,14,17 fatty acid, or both.

20. The method of claim 17, wherein the polypeptide comprises the amino acid sequence set forth in SEQ ID NO: 4.

* * * * *

SEQUENCE LISTING

<160> NUMBER OF SEQ ID NOS: 7

<210> SEQ ID NO 1
<211> LENGTH: 26
<212> TYPE: DNA
<213> ORGANISM: Eranthis hyemalis
<220> FEATURE:
<223> OTHER INFORMATION: primer sequence

<400> SEQUENCE: 1
tctagaatgg agtccatttc tgctag 26

<210> SEQ ID NO 2
<211> LENGTH: 28
<212> TYPE: DNA
<213> ORGANISM: Eranthis hyemalis
<220> FEATURE:
<223> OTHER INFORMATION: primer sequence

<400> SEQUENCE: 2
tctagattaa accagcttct tatccttg 28

<210> SEQ ID NO 3
<211> LENGTH: 949
<212> TYPE: DNA
<213> ORGANISM: Eranthis hyemalis
<220> FEATURE:
<223> OTHER INFORMATION: Coding region 25...852

<400> SEQUENCE: 3
atgcttcctt catttgtttc aaaaatggag tccatttctg ctagtgtacg ctactggcta 60
gtagaacacc cattggtgag cggattcgag tggatagaag gcgaaacatt tggttcatcg 120
ccaaaatttc ttctaaccac ggtagccacc tacctctccc taacctacat cctctccatc 180
acccttcttt caccgaaacc tccagtgaaa accccctcca agacccttac catcctccgg 240

```
tctatctccg caatacataa cctgattctc cttgccctct ccttcataat ggccttggga    300

gcgacattag caaccaccac caaaatgcca agcaagcaat ggatctgttt cccagcaaac    360

aaaacccgat cacagggtcc actatttttc tgggcttatg tgttctacct atccaagata    420

cttgaatacg tagataccct cttgatcatc ctccacaacg acgcaaggag actcacattt    480

ctccatgtct accatcacac tgttgttact atcatgtgtt acctttggct acacactaca    540

caatctctct tacctttggg gattgttacc aatgccaccg tgcatactgt catgtatgct    600

tattatttca tgtgcacact tgggaaaagg ccatcttgga agaggttagt gacagatttc    660

cagatcattc agttttggtt tggtctcggg atctccacgt tgatgttgtg gttccatttt    720

actggaactg gctgctctgg gatttgggga tggggttttt cttatgtctt caatgcttct    780

cttcttgctc tatttagtgc ttttcatgct aacaactacg ccaacaagga caaggataag    840

aagctggttt aactgcctat ttatggggtc tattcgtgtg gctatatcac catcccacgc    900

gatcagaatc tatttaggat atccttgtat caataagtta agtttgttt                949


<210> SEQ ID NO 4
<211> LENGTH: 275
<212> TYPE: PRT
<213> ORGANISM: Eranthis hyemalis

<400> SEQUENCE: 4

Met Glu Ser Ile Ser Ala Ser Val Arg Tyr Trp Leu Val Glu His Pro
1               5                   10                  15

Leu Val Ser Gly Phe Glu Trp Ile Glu Gly Glu Thr Phe Gly Ser Ser
            20                  25                  30

Pro Lys Phe Leu Leu Thr Thr Val Ala Thr Tyr Leu Ser Leu Thr Tyr
        35                  40                  45

Ile Leu Ser Ile Thr Leu Leu Ser Pro Lys Pro Pro Val Lys Thr Pro
    50                  55                  60

Ser Lys Thr Leu Thr Ile Leu Arg Ser Ile Ser Ala Ile His Asn Leu
65                  70                  75                  80

Ile Leu Leu Ala Leu Ser Phe Ile Met Ala Leu Gly Ala Thr Leu Ala
                85                  90                  95

Thr Thr Thr Lys Met Pro Ser Lys Gln Trp Ile Cys Phe Pro Ala Asn
            100                 105                 110

Lys Thr Arg Ser Gln Gly Pro Leu Phe Phe Trp Ala Tyr Val Phe Tyr
        115                 120                 125

Leu Ser Lys Ile Leu Glu Tyr Val Asp Thr Leu Leu Ile Ile Leu His
    130                 135                 140

Asn Asp Ala Arg Arg Leu Thr Phe Leu His Val Tyr His His Thr Val
145                 150                 155                 160

Val Thr Ile Met Cys Tyr Leu Trp Leu His Thr Thr Gln Ser Leu Leu
                165                 170                 175

Pro Leu Gly Ile Val Thr Asn Ala Thr Val His Thr Val Met Tyr Ala
            180                 185                 190

Tyr Tyr Phe Met Cys Thr Leu Gly Lys Arg Pro Ser Trp Lys Arg Leu
        195                 200                 205

Val Thr Asp Phe Gln Ile Ile Gln Phe Trp Phe Gly Leu Gly Ile Ser
    210                 215                 220

Thr Leu Met Leu Trp Phe His Phe Thr Gly Thr Gly Cys Ser Gly Ile
225                 230                 235                 240

Trp Gly Trp Gly Phe Ser Tyr Val Phe Asn Ala Ser Leu Leu Ala Leu
```

```
                245                 250                 255

Phe Ser Ala Phe His Ala Asn Asn Tyr Ala Asn Lys Asp Lys Asp Lys
            260                 265                 270

Lys Leu Val
        275


<210> SEQ ID NO 5
<211> LENGTH: 828
<212> TYPE: DNA
<213> ORGANISM: Eranthis hyemalis

<400> SEQUENCE: 5

atggagtcca tttctgctag tgtacgctac tggctagtag aacacccatt ggtgagcgga     60

ttcgagtgga tagaaggcga aacatttggt tcatcgccaa aatttcttct aaccacggta    120

gccacctacc tctccctaac ctacatcctc tccatcaccc ttctttcacc gaaacctcca    180

gtgaaaaccc cctccaagac ccttaccatc ctccggtcta tctccgcaat acataacctg    240

attctccttg ccctctcctt cataatggcc ttgggagcga cattagcaac caccaccaaa    300

atgccaagca agcaatggat ctgtttccca gcaaacaaaa cccgatcaca gggtccacta    360

tttttctggg cttatgtgtt ctacctatcc aagatacttg aatacgtaga taccctcttg    420

atcatcctcc acaacgacgc aaggagactc acatttctcc atgtctacca tcacactgtt    480

gttactatca tgtgttacct ttggctacac actacacaat ctctcttacc tttggggatt    540

gttaccaatg ccaccgtgca tactgtcatg tatgcttatt atttcatgtg cacacttggg    600

aaaaggccat cttggaagag gttagtgaca gatttccaga tcattcagtt ttggtttggt    660

ctcgggatct ccacgttgat gttgtggttc cattttactg gaactggctg ctctgggatt    720

tggggatggg gtttttctta tgtcttcaat gcttctcttc ttgctctatt tagtgctttt    780

catgctaaca actacgccaa caaggacaag gataagaagc tggtttaa                 828


<210> SEQ ID NO 6
<211> LENGTH: 829
<212> TYPE: DNA
<213> ORGANISM: Artificial Sequence
<220> FEATURE:
<223> OTHER INFORMATION: Codon-Optimized EhEL01 coding sequence

<400> SEQUENCE: 6

atggagtcca tctctgcaag cgtccgttat tggcttgtag agcacccact tgtgtcagga     60

ttcgagtgga tcgagggaga gacttttggt tcttctccaa aatttttgct gaccactgtg    120

gctacttatc tatcgttaac gtatattctg tccatcactc ttctctctcc taaaccgcct    180

gtcaaaacac cgtctaagac tcttacgatc ttaagatcta ttagcgctat tcacaacttg    240

atcttgttgg ctcttagttt tatcatggca cttggagcaa cattggcgac aactaccaag    300

atgcccagca agcaatggat ctgtttcccg gctaacaaga ccaggagcca gggtccattg    360

ttcttctggg catacgtttt ttatctaagt aaaatcctgg aatacgtcga taccctcctt    420

ataatcctcc acaacgacgc gaggagacta actttttttgc atgtgtatca ccacactgtg    480

gttaccatca tgtgttattt gtggcttcat actacccaat cacttttgcc cttaggaata    540

gttacaaacg ccacagtgca taccgtaatg tacgcttact acttcatgtg taccctggga    600

aaacgtccat cttggaagag actagtcaca gatttccaaa ttatccaatt ctggtttggt    660

ctcgggatct cgacccttat gctctggttt cacttcacag gcactggttg tagcggaatc    720

tggggttggg gattttcata cgtctttaac gcttccttgt tggctctatt cagtgctttc    780
```

```
catgcaaaca actacgccaa caaggacaag gataagaagc tagtctgat             829


<210> SEQ ID NO 7
<211> LENGTH: 990
<212> TYPE: DNA
<213> ORGANISM: Conidiobolus thromboides

<400> SEQUENCE: 7

atgagtttat taaatacatt ggatactatt acttcaagca ataatgttgt atcagcatac    60

aacgatgccc cagtagacta tttaattaaa gtagtagatt tagctttaac tgctaacaaa   120

gcagtcttca atgttataga agccaaagtt aacgtatgga tgccaacatt gatgataaac   180

ttaagagaac aggtctctaa tttaatctca ccaataagta aatacttgcc attgttagat   240

cctatcgaag tgttttctat cttgttttta tatatctttg ttgtgttttt ttggctcaaa   300

gtagcttcta gcttcctccc acgtttcgaa gtaagattat tttccctttt ccataatttc   360

tgtatggtcg ttttatccgc ctatatgtgc tcttccatcc tattacaagc ttatgcagat   420

aagtatattc tattcactaa ccccgtcgat cactctccaa atggtattcc aatggctaaa   480

ataatatggt tattttatat ttccaaaatc ccagagttcg ttgacactat gatcatgttg   540

gttaaacaaa actaccgcca aatctccttt ttacatgtct accatcatag ttcgatcttt   600

gctatttggt ggattgttac cttgatggca ccaaatggtg atgcttattt ctcagctgca   660

ttgaactcat ttattcatgt tgttatgtac ggatattatt tactctctgc acttggattc   720

aaatccgtct cctttgttaa gaaatatatt actatgggac aaatgactca atttgcactc   780

aactttgttc aagctagtta taatattgta gacagaaatt acttacgtcc acaagtccat   840

gagcaaggat tagcctatcc ttatgctctt tccgttttac tttggttcta tatgatctct   900

atgttggtgt tattcgctaa cttttatatt caagatcgta tccgtcaatc aaagttaaag   960

tctcaacaaa agggaaagaa aatgaattag                                   990
```